US008685421B2

(12) United States Patent
Kloke et al.

(10) Patent No.: US 8,685,421 B2
(45) Date of Patent: Apr. 1, 2014

(54) BEADED WOUND SPACER DEVICE

(75) Inventors: Tim M. Kloke, Victoria, MN (US); Steven J. Keough, St. Paul, MN (US); Nathan Lockwood, Minneapolis, MN (US); Margaret R. Gardner, Minneapolis, MN (US); Robert W. Hergenrother, Eden Prairie, MN (US); Ralph A. Chappa, Ham Lake, MN (US)

(73) Assignee: SurModics, Inc., Eden Prairie, MN (US)

( * ) Notice: Subject to any disclaimer, the term of this patent is extended or adjusted under 35 U.S.C. 154(b) by 1238 days.

(21) Appl. No.: 11/774,495

(22) Filed: Jul. 6, 2007

(65) Prior Publication Data

US 2008/0188819 A1 Aug. 7, 2008

Related U.S. Application Data

(60) Provisional application No. 60/806,727, filed on Jul. 7, 2006, provisional application No. 60/827,595, filed on Sep. 29, 2006, provisional application No. 60/863,572, filed on Oct. 30, 2006, provisional application No. 60/870,092, filed on Dec. 14, 2006, provisional application No. 60/889,534, filed on Feb. 12, 2007.

(51) Int. Cl.
*A01N 25/34* (2006.01)
*A61F 13/00* (2006.01)

(52) U.S. Cl.
USPC .......................................... 424/404; 604/304

(58) Field of Classification Search
USPC ............................................. 424/404
See application file for complete search history.

(56) References Cited

U.S. PATENT DOCUMENTS

| | | |
|---|---|---|
| 457,390 A | 8/1891 | Weeks |
| 3,030,951 A | 4/1962 | Mandarino |
| 3,095,877 A | 7/1963 | Rowan |
| 3,882,858 A * | 5/1975 | Klemm ............................ 606/76 |
| 3,915,955 A | 10/1975 | Cooper et al. |
| 3,987,497 A * | 10/1976 | Stoy et al. .................. 623/13.15 |
| 4,036,622 A | 7/1977 | Carroll et al. |
| 4,059,684 A | 11/1977 | Gross et al. |
| 4,191,740 A | 3/1980 | Heusser et al. |
| 4,191,743 A | 3/1980 | Klemm et al. |
| 4,233,287 A | 11/1980 | Heusser et al. |
| 4,329,743 A | 5/1982 | Alexander et al. |
| 4,347,841 A | 9/1982 | Benyo et al. |
| 4,373,217 A | 2/1983 | Draenert |
| 4,373,519 A | 2/1983 | Errede et al. |
| 4,440,750 A | 4/1984 | Glowacki et al. |
| 4,456,711 A | 6/1984 | Pietsch et al. |
| 4,460,642 A | 7/1984 | Errede et al. |
| 4,500,658 A | 2/1985 | Fox |
| 4,535,485 A | 8/1985 | Ashman et al. |
| 4,547,390 A | 10/1985 | Ashman et al. |
| 4,563,489 A | 1/1986 | Urist |
| 4,563,502 A | 1/1986 | Liu |
| 4,575,539 A | 3/1986 | DeCrosta et al. |
| 4,613,502 A | 9/1986 | Turková et al. |
| 4,619,655 A | 10/1986 | Hanker et al. |
| 4,791,150 A | 12/1988 | Braden et al. |
| 4,837,285 A | 6/1989 | Berg et al. |
| 4,853,225 A | 8/1989 | Wahlig et al. |
| 4,863,444 A | 9/1989 | Blomer |
| 4,881,546 A | 11/1989 | Kaessmann |
| 4,892,516 A | 1/1990 | Harle |
| 4,900,546 A | 2/1990 | Posey-Dowty et al. |
| 4,933,034 A | 6/1990 | Kokubu et al. |
| 4,960,415 A | 10/1990 | Reinmuller |
| 4,963,151 A | 10/1990 | Ducheyne et al. |
| 5,031,608 A | 7/1991 | Weinstein |
| 5,037,445 A | 8/1991 | Sander et al. |
| 5,055,307 A | 10/1991 | Tsuru et al. |
| 5,073,373 A | 12/1991 | O'Leary et al. |
| 5,100,490 A | 3/1992 | Holroyd et al. |
| 5,106,614 A | 4/1992 | Posey-Dowty et al. |
| 5,114,512 A | 5/1992 | Holroyd et al. |
| 5,154,951 A | 10/1992 | Finnicum et al. |
| 5,156,961 A | 10/1992 | Inoue et al. |
| 5,164,036 A | 11/1992 | Abe |
| 5,190,748 A | 3/1993 | Bachynsky et al. |
| 5,248,732 A | 9/1993 | Drzewinski |

(Continued)

FOREIGN PATENT DOCUMENTS

| | | |
|---|---|---|
| CN | 1048157 | 1/1991 |
| DE | 3037270 | 5/1982 |

(Continued)

OTHER PUBLICATIONS

STIC search results for chemical name and molecular information for tetrakis(4-benzophenylmethoxymethyl)methane.*
Cassas, M.D., Kyle J. et al., "Childhood and Adolescent Sports-Related Overuse Injuries", *American Family Physicians*, vol. 73, No. 6 Mar. 15, 2006 , 1014-1021.
Deslouches, B. et al., "Activity of the De Novo Engineered Antimicrobial Peptide WLBU2 Against *Pseudomonas aeruginosa* in Human Serum and Whole Blood: Implications for Systemic Applications", *J. Antimicrobial Agents & Chemotherapy* 2005 , 49(8): 3208-3216.
Eriksson, Ejnar , "Achilles tendon surgery and wound healing", *Knee Surg. Sports Traumatol, Arthrosc.*, 9:193 Editorial, Published online; May 23, 2001, 1 page.

(Continued)

*Primary Examiner* — Janet Epps-Smith
*Assistant Examiner* — Audrea Buckley
(74) *Attorney, Agent, or Firm* — Pauly, Devries Smith & Deffner LLC.

(57) ABSTRACT

A wound spacer device comprising multiple beads connected by non-absorbable suture material is disclosed. The device can be applied, for example, by a first responder to an injured individual, or can be applied by a trauma treatment facility, such as a Level 2 medical unit. In typical embodiments the device allows for site-specific controlled elution of an antimicrobial agent, such as Tobramycin, including defined elution over a period of time, such as 48 or 72 hours.

28 Claims, 14 Drawing Sheets

(56) References Cited

U.S. PATENT DOCUMENTS

| | | | |
|---|---|---|---|
| 5,258,291 A | 11/1993 | Inoue et al. | |
| 5,268,178 A | 12/1993 | Calhoun et al. | |
| 5,281,419 A | 1/1994 | Tuan et al. | |
| 5,328,533 A | 7/1994 | Yasuno et al. | |
| 5,334,626 A | 8/1994 | Lin | |
| 5,344,452 A | 9/1994 | Lemperle et al. | |
| 5,414,075 A | 5/1995 | Swan et al. | |
| 5,447,505 A | 9/1995 | Valentine et al. | |
| 5,470,625 A | 11/1995 | Perrault | |
| 5,486,593 A | 1/1996 | Tang et al. | |
| 5,487,899 A | 1/1996 | Davis | |
| 5,512,610 A | 4/1996 | Lin | |
| 5,582,838 A | 12/1996 | Rork | |
| 5,624,411 A * | 4/1997 | Tuch | 604/265 |
| 5,629,009 A | 5/1997 | Laurencin et al. | |
| 5,641,514 A | 6/1997 | Cho | |
| 5,665,109 A | 9/1997 | Yoon | |
| 5,667,501 A | 9/1997 | Fowler et al. | |
| 5,714,577 A | 2/1998 | Montelaro et al. | |
| 5,716,337 A * | 2/1998 | McCabe et al. | 602/49 |
| 5,733,545 A | 3/1998 | Hood, III | |
| 5,749,602 A | 5/1998 | Delaney et al. | |
| 5,755,787 A | 5/1998 | Camprasse et al. | |
| 5,756,127 A | 5/1998 | Grisoni et al. | |
| 5,833,642 A | 11/1998 | McCabe et al. | |
| 5,859,150 A | 1/1999 | Jamiolkowski et al. | |
| 5,882,858 A | 3/1999 | Dalla-Favera et al. | |
| 5,902,839 A | 5/1999 | Lautenschlager et al. | |
| 5,906,205 A | 5/1999 | Hiebert | |
| 5,919,477 A | 7/1999 | Bevan et al. | |
| 5,935,595 A | 8/1999 | Steen | |
| 5,945,507 A | 8/1999 | Montelaro et al. | |
| 5,958,465 A | 9/1999 | Klemm et al. | |
| 5,972,366 A | 10/1999 | Haynes et al. | |
| 6,020,396 A | 2/2000 | Jacobs | |
| 6,106,495 A | 8/2000 | Scott et al. | |
| 6,110,483 A * | 8/2000 | Whitbourne et al. | 424/423 |
| 6,156,330 A | 12/2000 | Tsukada et al. | |
| 6,197,330 B1 | 3/2001 | Rees et al. | |
| 6,214,901 B1 * | 4/2001 | Chudzik et al. | 523/113 |
| 6,242,995 B1 | 6/2001 | Shikama et al. | |
| 6,264,780 B1 | 7/2001 | Iwanaga et al. | |
| 6,299,898 B2 | 10/2001 | Rees et al. | |
| 6,309,669 B1 | 10/2001 | Setterstrom et al. | |
| 6,344,035 B1 | 2/2002 | Chudzik et al. | |
| 6,355,705 B1 | 3/2002 | Bond et al. | |
| 6,361,731 B1 | 3/2002 | Smith et al. | |
| 6,391,336 B1 | 5/2002 | Royer | |
| 6,413,342 B1 | 7/2002 | Yun et al. | |
| 6,413,539 B1 | 7/2002 | Shalaby | |
| 6,492,471 B1 | 12/2002 | Eisenbeiss et al. | |
| 6,495,127 B1 | 12/2002 | Wallace et al. | |
| 6,500,861 B1 | 12/2002 | Wider | |
| 6,503,267 B2 | 1/2003 | Bonutti et al. | |
| 6,503,539 B2 | 1/2003 | Gestrelius et al. | |
| 6,530,934 B1 | 3/2003 | Jacobsen et al. | |
| 6,531,146 B2 | 3/2003 | Calhoun et al. | |
| 6,576,263 B2 | 6/2003 | Truong et al. | |
| 6,579,533 B1 | 6/2003 | Tormala et al. | |
| 6,582,696 B2 | 6/2003 | Kuri-Harcuch et al. | |
| 6,582,713 B2 | 6/2003 | Newell et al. | |
| 6,630,486 B1 | 10/2003 | Royer et al. | |
| 6,656,488 B2 | 12/2003 | Yi et al. | |
| 6,673,362 B2 | 1/2004 | Calhoun et al. | |
| 6,689,153 B1 | 2/2004 | Skiba | |
| 6,692,510 B2 | 2/2004 | West | |
| 6,700,032 B1 | 3/2004 | Gray | |
| 6,713,083 B1 | 3/2004 | McGregor et al. | |
| 6,720,009 B2 | 4/2004 | Gestrelius et al. | |
| 6,835,713 B2 | 12/2004 | Mietzner et al. | |
| 6,869,976 B2 | 3/2005 | Royer | |
| 6,887,847 B2 | 5/2005 | Montelaro et al. | |
| 6,890,583 B2 | 5/2005 | Chudzik et al. | |
| 6,902,743 B1 | 6/2005 | Setterstrom et al. | |
| 6,908,065 B1 | 6/2005 | Ritchie | |
| 6,942,877 B2 | 9/2005 | Vogt et al. | |
| 6,979,324 B2 | 12/2005 | Bybordi et al. | |
| 6,998,510 B2 | 2/2006 | Buckman et al. | |
| 7,008,667 B2 | 3/2006 | Chudzik et al. | |
| 7,070,609 B2 | 7/2006 | West | |
| 7,097,850 B2 | 8/2006 | Chappa et al. | |
| 7,131,997 B2 | 11/2006 | Bourne et al. | |
| 2001/0001039 A1 | 5/2001 | Rees et al. | |
| 2002/0001609 A1 | 1/2002 | Calhoun et al. | |
| 2002/0018795 A1 | 2/2002 | Whitbourne et al. | |
| 2002/0172709 A1 | 11/2002 | Nielsen et al. | |
| 2002/0183265 A1 | 12/2002 | Vogt et al. | |
| 2002/0192191 A1 | 12/2002 | Kuri-Harcuch et al. | |
| 2004/0009228 A1 | 1/2004 | Tormala et al. | |
| 2004/0033251 A1 | 2/2004 | Sparer et al. | |
| 2004/0047891 A1 | 3/2004 | Glozman et al. | |
| 2004/0105880 A1 | 6/2004 | Turner et al. | |
| 2004/0115273 A1 | 6/2004 | Sparer et al. | |
| 2004/0116511 A1 | 6/2004 | Malik | |
| 2004/0121290 A1 | 6/2004 | Minevski et al. | |
| 2004/0127978 A1 | 7/2004 | Sparer et al. | |
| 2004/0193187 A1 | 9/2004 | Boehringer et al. | |
| 2004/0208934 A1 | 10/2004 | Royer | |
| 2004/0247644 A1 | 12/2004 | Bratt et al. | |
| 2004/0259949 A1 | 12/2004 | Klaveness et al. | |
| 2004/0265371 A1 | 12/2004 | Looney et al. | |
| 2005/0058767 A1 | 3/2005 | Bolton et al. | |
| 2005/0064009 A1 | 3/2005 | Bates | |
| 2005/0070835 A1 | 3/2005 | Joshi | |
| 2005/0145320 A1 | 7/2005 | Niwa | |
| 2005/0208134 A1 | 9/2005 | Magdassi et al. | |
| 2005/0218541 A1 | 10/2005 | Peng et al. | |
| 2005/0233475 A1 | 10/2005 | Wang et al. | |
| 2005/0241535 A1 | 11/2005 | Bohner | |
| 2005/0260246 A1 | 11/2005 | Chudzik et al. | |
| 2005/0271604 A1 | 12/2005 | Gestrelius et al. | |
| 2005/0281858 A1 | 12/2005 | Kloke et al. | |
| 2006/0024357 A1 | 2/2006 | Carpenter et al. | |
| 2006/0029637 A1 | 2/2006 | Tice et al. | |
| 2006/0030669 A1 | 2/2006 | Taton et al. | |
| 2006/0057224 A1 | 3/2006 | Hynes | |
| 2006/0100531 A1 | 5/2006 | Moser | |
| 2006/0106967 A1 | 5/2006 | Brocco et al. | |
| 2006/0188486 A1 | 8/2006 | Carpenter et al. | |
| 2006/0240072 A1 | 10/2006 | Chudzik et al. | |
| 2007/0010775 A1 | 1/2007 | Lutri | |
| 2007/0016163 A1 | 1/2007 | Santini et al. | |
| 2007/0026037 A1 | 2/2007 | Kloke et al. | |
| 2007/0026052 A1 | 2/2007 | Baggett | |
| 2007/0048350 A1 | 3/2007 | Falotico et al. | |
| 2007/0077280 A1 | 4/2007 | Collinge et al. | |
| 2007/0088370 A1 | 4/2007 | Kahle et al. | |
| 2012/0021038 A1 | 1/2012 | Kloke et al. | |

FOREIGN PATENT DOCUMENTS

| | | |
|---|---|---|
| EP | 0157909 | 10/1985 |
| EP | 0575090 | 12/1993 |
| EP | 0888785 | 1/1999 |
| EP | 0852148 | 2/2002 |
| EP | 1340476 | 9/2003 |
| EP | 1493451 | 1/2005 |
| EP | 1265550 | 5/2005 |
| EP | 1588675 | 10/2005 |
| FR | 2757528 | 6/1998 |
| JP | 53-61188 | 6/1978 |
| JP | 53-93687 | 8/1978 |
| JP | 53-0936787 A | 8/1978 |
| JP | 57-004915 | 1/1982 |
| JP | 60-156468 | 8/1985 |
| JP | 63-103809 | 5/1988 |
| JP | 01-093444 | 4/1989 |
| JP | 04-189352 | 7/1992 |
| JP | 05-078233 | 3/1993 |
| JP | 05-305134 | 11/1993 |
| JP | 06-178801 | 6/1994 |
| JP | 07-017851 | 1/1995 |
| JP | 07-039578 | 2/1995 |
| JP | 07-227171 | 8/1995 |

(56) References Cited

FOREIGN PATENT DOCUMENTS

| | | |
|---|---|---|
| JP | 07-308374 | 11/1995 |
| JP | 9-262278 | 2/1998 |
| JP | 10-045608 | 2/1998 |
| JP | 10-158075 | 6/1998 |
| JP | 11-029374 | 2/1999 |
| JP | 11-076293 | 3/1999 |
| JP | 2002165827 | 6/2002 |
| JP | 2002-249373 | 9/2002 |
| JP | 2003-062057 | 3/2003 |
| JP | 2005-015484 | 1/2005 |
| KR | 2000-0040011 | 7/2000 |
| KR | 2002-0041927 | 6/2002 |
| WO | WO 82/03174 | 9/1982 |
| WO | WO-82/03174 | 9/1982 |
| WO | WO-93/01841 | 2/1993 |
| WO | WO-00/24378 | 5/2000 |
| WO | WO-02/067849 | 9/2002 |
| WO | WO-03/070135 | 8/2003 |
| WO | WO-2004/022000 | 3/2004 |
| WO | WO-2005/007077 | 1/2005 |
| WO | WO-2006/005939 | 1/2006 |
| WO | WO-2006/031965 | 3/2006 |
| WO | WO-2006/119256 | 11/2006 |
| WO | WO-2007/016405 | 2/2007 |
| WO | WO-2007/027849 | 3/2007 |

OTHER PUBLICATIONS

Greene, Thomas L. et al., "Soft Tissue Coverage for Lower-Extremity Trauma: Current Practice and Techniques", *Journal of Orthopaedic Trauma*, vol. 2, No. 2 1988, 158-173.

Kakiuchi, Masaaki, "A Combined Open and Percutaneous Technique for Repair of Tendo Achillis", *The Journal of Bone and Joint Surgery*, vol. 77-B, No. 1 Jan. 1995, 60-63.

Lindhold, Ake, "A New Method of Operation in Subcutaneous Rapture of the Achilles Tendon", *Acta Chir. scandinav.* 117 1959, 261-270.

Maffulli, Nicola et al., "Early Weightbearing and Ankle Mobilization after Open Repair of Acute Midsubstance Tears of the Achilles Tendon", *The American Journal of Sports Medicine*, vol. 31, No. 5 2003, 692-700.

Movin, Tomas et al., "Acute Rupture of the Achilles Tendon", *Foot Ankle Clin N Am*, vol. 10, No. 2 Jun. 2005, 331-356.

Phadke, S. M. et al., "Lentivirus Lytic Peptide 1 Perturbs Outer and Inner Membrane of Serratia Marcescens", *J. Antimicrobial Agents & Chemotherapy* 2002, 46(6): 2041-2045.

Phadke, S. M. et al., "Selective Toxicity of Engineered Lentivirus Lytic Peptides in a CF Airway Cell Model", *Peptides* 2003, 24: 1099-1107.

Tencza, S. B. et al., "Lentivirus-Derived Antimicrobial Peptides: Increased Potency by Sequence Engineering and Dimerizaion", *J. Antimicrobial Agents & Chemotherapy* 1999, 44(1): 33-41.

Tencza, S. B. et al., "Novel Antimicrobial Peptides Derived From Human Immunodeficiency Virus Type 1 and Other Lentivirus Transmembrane Proteins", *J. Antimicrobial Agents & Chemotherapy* 1997, 41(11): 2394-2398.

Young, Jonathan S. et al., "Achilles Tendon Rupture and Tendinopathy: Management of Complications," *Foot Ankle Clin N Am*, 10 (2005) pp. 371-382.

Adams, Kenneth et al., "In Vitro and in Vivo Evaluation of Antibiotic Diffusion from Antibiotic-Impregnated Polymethylmethacrylate Beads", *Clinical Orthopaedics and Related Research*, No. 278 May 1992, 244-252.

Alpern, Eytan J., "In Vitro Elution Characteristics of Tobramycin and Vancomycin Release from Locally Implantable Biodegradable Sponges", *Market Research, An Alternate Technology*, htto://www.hwbf.org/ota/am/ota99/otapo/OTP99029.htm Jul. 18, 2006, 2 pages.

Alpert, Brian et al., "The In Vivo Behavior of Gentamicin-PMMA Beads in the Maxillofacial Region", *J. Oral Maxillofac. Surg.*, vol. 47, 1989, 46-49.

"Septopal", *Biomet Europe* http://www.biometeurope.com/index.php?id=232, 1-5 (web).

Bowyer, G W., "Antibiotic impregnated beads in open fractures. A report on the technique and possible applications in military surgery", *J R Army Medical Corps*, 139(3):100-4.Links Abstract only Oct. 1993, 2 pages.

Bowyer, Gavin W. et al., "Antibiotic Release from Impregnated Pellets and Beads", *The Journal of Trauma*, vol. 36, No. 3 Mar. 1994, 331-335.

Buranapanitkit, Boonsin et al., "In Vitro inhibitive effect of antibiotic beads to common orthopaedic pathogens: Home-made vs. commercial beads", *The Thai J of Orthop Surg*, 25(2): 48-52 Abstract, http://medinfo.psu.ac.th/AnnualResearch/2000/bboo1.htm 2000, 1 page.

Burd, Timothy A. et al., "In Vitro Elution of Tobramycin from Bioabsorbable Polycaprolactone Beads", *Journal of Orthopaedic Trauma*, vol. 15, No. 6 2001, 424-428.

Butson, R. J. et al., "Treatment of intrasynovial infection with gentamicin-impregnated polymethylmethacrylate beads", *The Veterinary Record*, No. 138 May 11, 1996, 460-464.

Calhoun, Jason H. et al., "Antibiotic Beads in the Management of Surgical Infections", *The American Journal of Surgery*, vol. 157 Apr. 1989, 443-449.

Calhoun, Jason H. et al., "The Treatment of Infected Nonunions with Gentamicin-Polymethylmethacrylate Antibiotic Beads", *Clinical Orthopaedics and Related Research*, No. 295 Oct. 1993, 23-27.

Calhoun, M.D., Jason, "Antibiotics and War Wounds", *Extremity War Injuries; State of the Art and Future Directions, Presentation Abstracts, Session III: Antibiotics and Infections: Moderators Overview*, 14 Undated, 1 page.

Campoccia, Davide et al., "The significance of infection related to orthopedic devices and issues of an antibiotic resistance", *Biomaterials 27* 2006, 2331-2339.

Celikoz, B. et al., "Subacute reconstruction of lower leg and foot defects due to high velocity-high energy injuries caused by gunshots, missiles, and land mines", *Microsurgery*: 25(1):3-14; discussion 15 Abstract from www.pubmed.gov 2005, 2 pages.

Cierny, III, George et al., "Treatment of Chronic Infection", *J Am Acad Orthop Surg*, vol. 14, No. 10 Sep. 2006, S105-S110.

Clasper, J., "The interaction of projectiles with tissues and the management of ballistic fractures", *J R Army Med Corps*; 147(1):52-61 Abstract, from www.pubmed.gov Feb. 2001, 1 page.

Class II Special Controls Guidance Document: Polymethylmethacrylate (PMMA) Bone Cement; Guidance for Industry and FDA, Center for Devices and Radiological Health, Jul. 17, 2002, pp. 1-18.

"Controversies in the Treatment of Open Tibial Fractures," *Advanceds in the Treatment of Tibial Shaft Fractures: A Current Concepts Review*, from Medscape website, printed May 7, 2007.

Covey, M.D., Dana C., "Compat orthopaedics: A View From the Trenches", *J Am Acad Orthop Surg*, vol. 14, No. 10 Sep. 2006, S10-S17.

Davis, Kepler A. et al., "Multidrug-Resistant *Acinetobachter* Extremity Infections in Solders," *Emerging Infectious Diseases*, www.cdc.gov/eid, vol. 11. No. 8, Aug. 2005, pp. 1218-1224.

Decoster, M.D., Thomas A. et al., "Preparation and Use of Antibiotic-Impregnated Beads for Orthopaedic Infections", *Abstract only* Undated, 1 page.

Dierks, Eric J. et al., "Treatment of an Infected Mandibular Graft Using Tobramycin-Impregnated Methylmethacrylate Beads: Report of a Case", *Journal of Oral and Maxillofacial Surgery*, vol. 50, No. 11 Nov. 1992, 1243-1245.

Dullea, Mark, "C-077R Markets for Advanced Wound Care Technologies," http://www.bccresearch.com/biotech/C0774.html., May 1, 2006, pp. 1-16.

Eckman, Jr., James B. et al., "Wound and Serum Levels of Tobramycin With the Prophylactic Use of Tobramycin-Impregnated Polymethylmethacrylate Beads in Compound Fractures", *Clinical Orthopaedics and Related Research*, No. 237 Dec. 1988, 213-215.

Ensing, G. T. et al., "Differences in Structure Between Antibiotic-Loaded Bone Cements (Palacos R-Ga nd Copal) and Beads (Septopal) Prior to and After Antibiotic Release", *Structure of Antibiotic-Loaded Bone Cements and Beads* Unknown, 69-80.

(56) References Cited

OTHER PUBLICATIONS

Evans, Richard P. et al., "Gentamicin-Impregnated Polymethylmethacrylate Beads Compared with System Antibiotic Therapy in the Treatment of Chronic Osteomyelitis", *Clinical Orthopaedics and Related Research*, No. 295 Oct. 1993, 37-42.

Faber, Christopher et al., "In vivo comparison of Dhvar-5 and gentamicin in an MRSA osteomyelitis prevention model", *Journal of Antimicrobial Chemotherapy* 2004, pp. 1-14.

Faber, Christopher, *Histatin and lactoferrin-derived antimicrobial peptides*; in vitro *and* in vivo *studies on the treatment and prevention of osteomyelitis*, "Table of Contents and Chapter 1, General Introduction and Reference List," 19 pages, 2007, Amsterdam.

Faber, Christopher, *Histatin and lactoferrin-derived antimicrobial peptides*; in vitro *and* in vivo *studies on the treatment and prevention of osteomyelitis*, "Chapter 2, Release of the antimicrobial peptide Dhvar-5 from polymethyl methacrylate beads, and Reference List," 14 pages, 2007.

Faber, Christopher, *Histatin and lactoferrin-derived antimicrobial peptides*; in vitro *and* in vivo *studies on the treatment and prevention of osteomyelitis*, "Chapter 3, Simultaneous release of Dhvar-5 and gentamicin from PMMA beads, and Reference List," 10 pages, 2007.

Faber, Christopher, *Histatin and lactoferrin-derived antimicrobial peptides*; in vitro *and* in vivo *studies on the treatment and prevention of osteomyelitis*, "Chapter 4, Mechanical and architectural properties of PMMA bone cement containing Dhvar-5 and/or gentamicin, and Reference List," 15 pages, 2007.

Faber, Christopher, *Histatin and lactoferrin-derived antimicrobial peptides*; in vitro *and* in vivo *studies on the treatment and prevention of osteomyelitis*, "Chapter 5, in vivo comparison of Dhvar-5 and gentamicin in an MRSA osteomyelitis prevention model, and Reference List," 20 pages, 2007.

Faber, Christopher, *Histatin and lactoferrin-derived antimicrobial peptides*; in vitro *and* in vivo *studies on the treatment and prevention of osteomyelitis*, "Chapter 6, Comparable efficacy of antimicrobial peptide, human Lactoferrin 1-11 and Gentamicin in a chronic MRSA osteomyelitis, and Reference List," 20 pages, 2007.

Faber, Christopher, *Histatin and lactoferrin-derived antimicrobial peptides*; in vitro *and* in vivo *studies on the treatment and prevention of osteomyelitis*, "Chapter 7, General Discussion, Background, Discussion, and Reference List," 11 pages, 2007.

Faber, Christopher, *Histatin and lactoferrin-derived antimicrobial peptides*; in vitro *and* in vivo *studies on the treatment and prevention of osteomyelitis*, "Chapter 8, Samenvatting en discussie, and Reference List," 12 pages, 2007.

Faber, Christopher, *Histatin and lactoferrin-derived antimicrobial peptides*; in vitro *and* in vivo *studies on the treatment and prevention of osteomyelitis*, "Appendices: Dankwoord, Publicatielijst, Curriculum Vitae and Abbrevations," 12 pages, 2007.

Farnsworth, Kelly D. et al., "The Effect of Implanting Gentamicin-Impregnated Polymethylmethacrylate Beads in the Tarsocrural Joint of the Horse", *Veterinary Surgery*, vol. 30 2001, 126-131.

Fernandex-Fairen, M.D., Mariano et al., "Augmented Repair of Achilles Tendon Ruptures", *The American Journal of Sports Medicine*, vol. 25, No. 2 1997, 177-181.

Flick, Arthur B. et al., "Noncommercial Fabrication of Antibioticimpregnated Polymethylmethacrylate Beads", *Clinical Orthopaedics and Related Research*, No. 223 Oct. 1987, 282-286.

Gitelis, Steven et al., "The Treatment of Chronic Osteomyelitis with a Biodegradable Antibiotic-Impregnated Implant", *Journal of Orthopaedic Surgery*, 10(1) 2002, 53-60.

Gonzalez, Della Valle A. et al., "Effective bactericidal activity of tobramycin and vancomycin eluted from acrylic bone cement", *Acta Orthop Scand*, 72 (3), 237-40. Abstract Jun. 2001, 1 page.

Goodell, John A. et al., "Preparation and release characteristics of tobramycin-impregnated polymethylmethacrylate beads", *American Journal of Hospital Pharmacy*, vol. 43 Jun. 1986, 1454-1461.

Gosselin, R. A. et al., Antibiotics for preventing infection in open limb fractures (Cochrane Review), Abstract, Oct. 13, 2009, pp. 1-2 from http://www.update-software.com/Abstracts/AB003764.htm, and www.pubmed.gov, pp. 1-8, Oct. 13, 2006.

Gruninger, M.D., Robert P. et al., "Chapter 8: Antibiotic-Impregnated PMMA Beads in Bone and Prosthetic Joint Infections", *Orthopaedic Infections*, Elsevier, 1989 1989, 66-74.

Gunderson, Brent W. et al., "Synergistic Activity of Colistin and Ceftazidime against Multiantibiotic-Resistant *Pseudomonas aeruginosa* in an in Vitro Pharmacodynamic Model", *Antimicrobial Agents and Chemotherapy*, vol. 47, No. 3 Mar. 2003 pp. 905-909.

Hain, M.D., Timothy C., "Gentamicin Toxicity", *Gentamicin Ototoxicity* http://www.dizziness-and-balance.com/disorders/bilat/gentamicin%20toxicity.htm May 4, 2006, pp. 1-9.

Hanssen, M.D., Arlen D. et al., "Local Antibiotic Delivery Systems, Where Are We and Where Are We Going?", *Clinical Orthopaedics and Related Research*, No. 437 Aug. 2005, pp. 111-114.

Hanssen, M.D., Arlen D., "Prophylactic Use of Antibiotic Bone Cement", *The Journal of Anthroplasty*, vol. 19, No. 4, Suppl. 1 2004, pp. 73-77.

Hanssen, M.D., Arlen D., "Session IV: Local Antibiotic Delivery Systems, Local Antibiotic Delivery Systems, Local Antibiotic Delivery Vehicles in the Treatment of Musculoskeletal Infection", *Clinical Orthopaedics and Related Research*, No. 437 Aug. 2005, pp. 91-96.

Hanssen, M.D., Arlen D. et al., "Treatment of the Infected Hip Replacement", *Clinic Orthop*, No. 420 Mar. 2004, pp. 63-71.

Hardy, Mark A., DPM, "Current Controversies in Podiatry, Antibiotic Therapy in Open Fractures," http://www.podiatryonline.com/patient_care/how_to/antibiotic.cfm., May 1, 2006, pp. 1-4.

Henry, Stephen L. et al., "Antibiotic-Impregnated Beads", *Orthopaedic Review*, vol. XX, No. 3 Mar. 1991, 242-247.

Henry, Stephen L. et al., "Local Antibacterial Therapy for the Management of Orthopeadic Infections", *Clinical Pharmacokinetics* 1995, 29(1): 36-45.

Henry, Stephen L. et al., "Long-Term Implantation of Gentamicin-Polymethylmethacrylate Antibiotic Beads", *Clinical Orthopaedics and Related Research*, No. 295 Oct. 1993, 47-53.

Henry, Stephen L. et al., "The Antibiotic Bead Pouch Technique", *Clinical Orthopaedics and Related Research*, No. 295 Oct. 1993, 54-62.

Henry, Stephen L. et al., "The Prophylactic Use of Antibiotic Impregnated Beads in Open Fractures", *The Journal of Trauma*, vol. 30, No. 10 Oct. 1990, 1231-1238.

Hettiaratchy, Shehan et al., "Pathophysiology and Types of Burns", *BMJ* Jun. 10, 2007, vol. 328: 1427-1429.

Hong, M.D., Joon P. et al., "The Use of Anterolateral Thigh Perforator Flaps in Chronic Osteomyelitis of the Lower Extremity", *Plastic & Reconstructive Surgery*, 115(1): 142-147 Abstract Jan. 2005, 1 page.

Hota, M.D., Bala et al., "Community-Associated Methicillin-Resistant *Staphylococcus aureus* Skin and Soft Tissue Infections at a Public Hospital, Do Public Housing and Incarceration Amplify Transmission?", *Arch Intern Med*, vol. 167 May 28, 2007, 1026-1033.

Keating, J. F. et al., "Reamed nailing of open tibial fractures: does the antibiotic bead pouch reduce teh deep infection rate?", *J Orthop Trauma*, 10(5): 298-303 Abstract from www.pubmed.gov 1996, 1 page.

Klemm, Klaus W., "Antibiotic Bead Chains", *Clinical Orthopaedics and Related Research*, No. 295 Oct. 1993, 63-76.

Klemm, K., "The use of antibiotic-containing bead chains in the treatment of chronic bone infections", *Clinical Microbiology and Infection*, vol. 7, No. 1 Jan. 2001, 28-31.

Krasko, Michal Y. et al., "Gentamicin extended release from an injectable polymeric implant", *Journal of Controlled Release*, 117 2007, pp. 90-96.

Kwan, Ng W. et al., "Melioidotic osteomyelitis treated with antibiotic-calcium hydroxyapatite composite: case report with four-year follow-up", *Signapore Med J*, 47(1) 2006, pp. 71-74.

Leone, M.D., James M. et al., "Management of Infection at the Site of a Total Knee Arthroplasty", *The Journal of Bone & Joint Surgery*, vol. e87-A, No. 10 Oct. 2005, pp. 2336-2348.

Lyons, Val O. et al., "Bacterial Adherence to Plain and Tobramycin-Laden Polymethylmethacrylate Beads", *Clinical Orthopaedics and Related Research*, No. 278 May 1992, 260-264.

(56) References Cited

OTHER PUBLICATIONS

Mader, Jon T. et al., "In Vitro Evaluation of Antibiotic Diffusion from Antibiotic-Impregnated Biodegradable", *Antimicrobial Agents and Chemotherapy*, vol. 41, No. 2 Feb. 1997, pp. 415-418.

Marculescu, M.D., C. E. et al., "Prosthetic Joint Infection Diagnosed Postoperatively by Intraoperative Culture", *Clinical Orthopaedics and Related Research*, No. 438 Oct. 2005, pp. 38-42.

Matsuno, H. et al., "Anbiotic-containing hyaluronic acid gel as an antibacterial carrier: Usefulness of sponge and film-formed HA gel in deep infection," UJ. Orthop Res., Jan. 6, 2006; 24(3): 321-326, pp. 1-2, downloaded May 11, 2006.

McHale, Kathleen A. et al., "Treatment of Infected Tibial Nonunions with Debridement, Antibiotic Beads, and the Ilizarov Method", *Military Medicine*, vol. 169 Sep. 2004, 728-734.

McLaren, M.D., A. C. et al., "Phenolphthalein Used to Assess Permeability of Antibiotic Laden PMMA—A Pilot Study", *Mulsculo Skeletal Infection Society*, 2004 Abstract: BS 5 http://www.msis-na.org/id83_m.htm May 1, 2006, pp. 1-2.

McNamara, M.D., David R. et al., "Advances in Therpaeutics and Diagnostics, Vancomycin", *J. Am. Acad. Orthop. Surg*, vol. 13, No. 2 2005, 89-92.

Miclan, T. et al., "Bone Toxicity of Locally Applied Aminoglycosides.", *Journal of Orthop. Trauma*, 1995; 9(5), pp. 1-2 from EntrezPubMed on the web.

"Military Service: A Mayo Clinic tradition," articles by John L. Black, M.D., Henry Schiller, M.D., Mark Sawyer, M.D., Paul Huddleston, M.D., and Brian McGlinch, M.D., *Mayo Alumni 2006*, pp. 2-7.

Moehring, M.D., H. D. et al., "Comparison of Antibiotic Beads and Intravenous Antibiotics in Open Fractures", *Clinical Orthopaedics and Related Research*, No. 372 2000, 257-261.

Mohanty, S. P. et al., "Use of Antibiotic-Loaded Polymethyl Methacrylate Beads in the Management of Musculosketal Sepsis—a Retrospective Study", *Journal of Orthopaedic Surgery*, vol. 11, No. 1 Jun. 2003, 73-79.

Naraharisetti, Pavan K. et al., "In Vitro and In Vivo Release of Gentamicin from Biodegradable Discs", *J Biomed Mater Res Part B: Appl Biomater* 77B 2006, pp. 329-337.

Nelson, Carl J. et al., "A Comparison of Gentamicin-Impregnated Polymethylmethacrylate Bead Implantation to Conventional Parenteral Antibiotic Therapy in Infected Total Hip and Knee Arthroplasty", *Clnical Orthopaedics and Related Research*, No. 295 Oct. 1993, 96-101.

Nelson, Carl L. et al., "In Vitro Elution Characteristics of Commercially and Noncommercially Prepared Antibiotic PMMA Beads", *Clinical Orthopaedics and Related Research*, No. 284 Nov. 1992, 303-309.

Neut, Danielle et al., "Biomaterial-associated infection of gentamicin-loaded PMMA beads in orthopaedic revision surgery", *Journal of Antimicrobial Chemotherapy*, No. 47 2001, 885-891.

Nix, David E. et al., "Antibiotic Tissue Penetration and its Relevance: Impact of Tissue Penetration on Infection Response", *Antimicrobial Agents and Chemotherapy*, vol. 35, No. 10 1991, 1953-1959.

Ostermann, Peter et al., "Local Antibiotic Therapy for Severe Open Fractures", *The Journal of Bone and Joint Surgery* Jan. 1995, vol. 77-B: 93-97.

Ostermann, Peter A. et al., "The Role of Local Antibiotic Therapy in the Management of Compound Fractures", *Clinical Orthopaedics and Related Research*, No. 295 Oct. 1993, 102-111.

Ostermann, Peter A. et al., "Timing of Wound Closure in Severe Compound Fractures", *Orthopedics*, vol. 17, No. 5 May 1994, 397-399.

Owen, M. R. et al., "Management of MRSA Septic B Arthritis in a Dog Using a Gentamicin Impregnated Collagen Sponge," *Journal of Small Animal Practice*, (2004), 45, pp. 1-11, http://tahilla.typepad.com/petsmrsa/2004/12/management_of_m.html, downloaded May 1, 2006.

Patel, M.D., Robin et al., "The Diagnosis of Prosthetic Joint Infection", *Clinical Orthopaedics and Related Research*, No. 437 Aug. 2005, pp. 55-58.

Patzakis, Michael J. et al., "Prospective, Randomized, Double-Blind Study Comparing Single-Agent Antibiotic Therapy, Ciprofloxacin to Combination Antibiotic Therapy in Open Fracture Wounds", *Journal of Orthopaedic Trauma*, vol. 14, No. 8 2000, pp. 529-533.

Perry, M.D., Archie C. et al., "Antimicrobial Release Kinetics from Polymethylmethacrylate in a Novel Continuous Flow Chamber", *Clinical Orthopaedics and Related Research* Oct. 2002, 3 pages.

Polly, Jr., David W. et al., "Advanced Medical Care for Soldiers Injured in Iraq and Afghanistan", *MMA Publication, Minnesota Medicine*, vol. 87 Nov. 2004, pp. 1-6.

Popham, G. J. et al., "Antibiotic-Impregnated Beads", *Orthopaedic Review*, vol. XX, No. 4 Apr. 1991, 331-337.

Roeder, Brett et al., "Antibiotic Beads in the Treatment of Diabetic Pedal Osteomyelitis", *The Journal of Foot & Ankle Surgery*, vol. 39, No. 2 Mar./Apr. 2000, 124-129.

Rotschafer, Pharmd, John et al., "In Vitro Characterization of Tobramycin Coated Beads Combined with Tobramycin-Sensitive and -Resistant Strains of *Acinetobacter baumannii, Pseudomonas aeruginosa, Staphylococcus aureus* and *Staphylococcus epidermidis*", PowerPoint presentation May 2007, pp. 1-27.

Schmidt, Andrew H., M.D., et al., "Pathophysiology of Inventions After Internal Fixation of Fractures," *J Am Acad Orthop Surg*, 2000, vol. 8, No. 5, Sep./Oct. 2000, pp. 285-291.

Scott, C. P., "Effectiveness of bone cement containing tobramycin: an in vitro susceptibility study of 99 organisms found in infected joint arthroplasty," *Journal of Bone and Joint SurgeryJournal of Bone and Joint Surgery*, pp. 1-6 from http://findarticles.com/p/articles/mi_ga3767/is_199905/ai_n8845754/print, Aug. 8, 2007.

Scott, David M. et al., "Use of Vancomycin and Trobramycin Polymethylmethacrylate Impregnated Beads in the Management of Chronic Osteomyelitis", *Drug Intelligence and Clinical Pharmacy*, vol. 22 Jun. 1988, 480-483.

Seeley, Stacy K. et al., "Volume and Surface Area Study of Tobramycin-Polymethylmethacrylate Beads", *Clin. Orthop.*, No. 420 Mar. 2004, 298-303.

Seligson, D. et al., "Antibiotic-leaching from polymethylmethacrylate beads", *The Journal of Bone & Joint Surgery*, vol. 75 1993, 714-720.

Seligson, David et al., "The Management of Open Fractures Associated with Arterial Injury Requiring Vascular Repair", *The Journal of Trauma*, vol. 37, No. 6 Dec. 1994, 938-940.

Seligson, David et al., "The Use of Antibiotic-Impregnated Polymethylmethacrylate Beads to Prevent the Evolution of Localized Infection", *Journal of Orthopaedic Trauma*, vol. 6, No. 4 1992, 401-406.

Sirkin, M., et al., "A staged protocol for soft tissue management in the treatment of complex pilon fractures," *J. Orthop Trauma*, Nov. 2001; 15(8): 591, http://www.ncbi.nlm.nih.gov/sites/entrez?cmd-Retrieve&db=PubMed&list_uids=10052780, pp. 1-2, downloaded Jul. 9, 2007.

Smith & Nephew, "Wound Bed Preparation," pp. 1-2, http://wound.smith-nephew.com/us/popup.asp?Nodeld-2630&Hide-True&Tab=, downloaded May 1, 2006.

Stevens, C. M. et al., "An articulated antibiotic spacer used for infected total knee arthroplasty: a comparative in vitro elution study of Simplex and Palacos bone cements," *J. Orthop. Res.*, Jan. 2005; 23(1):27-33; 1 page from http://www.ncbi.nim.nih.gov/entrez/query.fcgi?itool=abstractplus&db=pubmed&cmd, downloaded Aug. 9, 2006.

Stone, Patrick A. et al., "Use of Antibiotic-Loaded Polymethylmethacrylate Beads for the Treatment of Extracavitary Prosthetic Vascular Graft Infections", *Journal of Vascular Surgery*, vol. 44, No. 4 Oct. 2006, 757-761.

Suzuki, A. et al., "A biodegradable delivery system for antibiotics and recombinant human bone morphogenetic protein-2: A potential treatment for infected bone defects," *J. Orthop. Res.*, Mar. 2006; 24(3): 327-32, p. 1 from http://www.ncbi.nlm.nih.gov/sites/entrez?cmd-Retrieve&db=PubMed&list_uids-16479565., downloaded Jul. 9, 2007.

Templeman, David, M.D., "Advances in the Treatment of Tibial Shaft Fractures: a Current Concepts Review," pp. 1-15 from http://www.medscape.com;/viewprogram/248_pnt, downloaded Aug. 8, 2007.

(56) References Cited

OTHER PUBLICATIONS

Tornetta, Paul, III, M.D., et al., "The Use of Solid Form-Fitting Antibiotic Cement Spacers in Bone Loss of the Tibia," OTA 2004 Posters, pp. 1-2, Jul. 25, 2006.

Von Frauhofer, J. A. et al., "Leaching of tobramycin from PMMA bone cement beads", *Journal of Biomedical Materials Research*, vol. 19. 1985, pp. 751-756.

Wahlig, H., et al., "The Release of Gentamicin from Polymethylmethacrylate Beads," *The Journal of Bone and Joint Surgery*, vol. 60-B, No. 2, May 1978, pp. 270-275.

Walenkamp, Geert H. I. M., M.D., et al., "Gentamicin_PMMA Beads, Pharmacokinetic and Nephrotoxicological Study," *Clinical Orthopaedics and Related Research*, No. 205, Apr. 1986, 7 pages.

Wang, Gahin et al., "The release of cefazolin and gentamicin from biodegradable PLA/PGA beads," *International Journal of Pharmaceutics*, 273 (2004) 203-212.

Weitz-Marshall, Amanda D. et al., "Timing of Closure of Open Fractures", *Journal of the American Academy of Orthopaedic Surgeons*, vol. 10, No. 6 Nov./Dec. 2002, 379-383.

Wenke, J. C., et al., "Effectiveness of commercially-available antibioticimpregnated implants," *The Journal of Bone & Joint Surgery (Br)*, vol. 88-B, No. 8, Aug. 2006, pp. 1102-1104.

Wheeless' Textbook of Orthopaedics, "Addition of Antibiotics to Cement," from http://www.wheelessonline.com/ortho/comparison_of antibiotics_to_cement, pp. 1-3, downloaded May 10, 2006.

Wheeless' Textbook of Orthopaedics, "Comparison of the clinical efficacy and tolerance of gentamicin beads," from http://www.wheelessonline.com/ortho/comparison_of the_clinical_efficacy_and_tolerance, 1 page, downloaded May 10, 2006.

Wilson, Katharine J. et al., "Comparative Evaluation of the Diffusion of Tobramycin and Cefotaxime Out of Antibiotic-Impregnated Polymethylmethacrylate Beads", *Journal of Orthopaedic Research*, vol. 6, No. 2 1988, 278-286.

Wininger, David A. et al., "Antibiotic-Impregnated Cement and Beads for Orthopedic Infections", *Antimicrobial Agents and Chemotherapy*, vol. 40, No. 12 Dec. 1996, 2675-2679.

Wu, P. et al., "Orthopedic device-based drug delivery," Article in Press, Biomaterials, date unknown, pp. 1-3.

Wu, Peng et al., "Drug/device combinations for local drug therapies and infection prophylaxis", *Biomaterials* 27 2006, 2450-2467.

Yung, Anthony C. et al., "Diabetes Watch: Can Antibiotic Beads Have an Impact in Osteomyelitis Cases?", *Podiatry Today* Oct. 2003, Issue 10: 14-18. pp. 1-7, from web, downloaded May 7, 2007.

Zalavras, Charalampos G., M.D., et al., "Open Fractures: Evaluation and Management," *Journal of the American Academy of Orthopaedic Surgeons*, vol. 11, No. 3, May/Jun. 2003, pp. 212-219.

Zalavras, Charalampos G., M.D., et al., "Local Antibiotic Therapy in the Treatment of Open Fractures and Osteomyelitis," *Clinical Orthopaedics and Related Research*, No. 427, Oct. 2004, pp. 86-93.

Zellweger, G. et al., "Infection in the Upper Body: Hand and Burn-Wound Microbiology and Considerations for Antimicrobial Therapy", *Journal of Burn Care & Rehabilitation*, vol. 13, No. 2, Part 2 Mar./Apr. 1992, 298-304.

Blaha, J. D. "Comparison of the clinical efficacy and tolerance of gentamicin PMMA beads on surgical wire versus combined and systemic therapy for osteomyelitis," *Clin Orthop Relat Res*. (295):8-12 (Abstract Only) Oct. 1993, 1 page.

Fish, D. N. "Antibiotic-impregnated cement use in U.S. hospitals," *Am J Hosp. Pharm*. 49(10):2469-74 (Abstract only) Oct. 1992, 1 page.

Hofmann, A. A. "Treatment of Infected Total Knee Arthroplasty Using an Articulating Spacer," *Clin Orthop Relat Res*, 321:45-54 Abstract Only Dec. 1995, 1 page.

Sayegh, Ayman I. "Polymethylmethacrylate Beads for Treating Orthopedic Infections," *Copendiium*, vol. 25(10) 2003, 788-795.

Cunningham, Amy "Antibiotic Bead Production," 35 2000, 31-35. *Iowa Orthopaedic J*, 20:31-35 2000, 31-35.

Bayston, R. "The Sustained Release of Antimicrobial Drugs from Bone Cement," *J. Bone Joint Surg*, 64-B:460. 1982, 460-464.

McNamara, M.D., David R. et al., "Advances in Therapeutics and Diagnostics, Vancomycin," *J. Am. Acad. Orthop. Surg*. vol. 13, No. 2 2005, 89-92.

Calhoun, M.D., Jason, "Antibiotics and War Wounds," *Extremity War Injuries; State of the Art and Future Directions, Presentation Abstracts, Session III: Antibiotics and Infections: Moderators Overview*, 14, 2006, 1 page.

Decoster, M.D., Thomas A. et al., "Preparation and Use Antibiotic-Impregnated Beads for Orthopaedic Infections", Abstract only, 2008, 1 page.

Ensing, G. T. et al., "Differences in Structure Between Antibiotic-Loaded Bone Cements (Palacos R-Ga nd Copal) and Beads (Septopal) Prior to and After Antibiotic Release", *Structure of Antibiotic-Loaded Bone Cements and Bead* 2006, 69-80.

Pollak, Andrew N. et al., "Extremity War Injuries: State of the Art and Future Directions, Prioritized Future Research Objectives," *Journal of the American Academy of Orthopaedic Surgeons*, vol. 14, No. 10, 2006, pp. S212-S214.

"Septopal", *Biomet Europe* http://www.biometeurope.com/index.php?id=232, Oct. 30, 2007, 1-5 (web).

Wu, P. et al., Drug/device combinations for local drug therapies and infection prophylaxis, Section 7, "Orthopedic device-based drug delivery," Article in Press, Biomaterials, vol. 27, Issue 11, Apr. 2006, pp. 2450-2467.

Non Final Office Action mailed Jun. 28, 2011 in co pending U.S. Appl. No. 12/349,312, "Medical Device with Coating Composition" (34 pages).

File History of U.S. Appl. No. 13/242,837, filed Sep. 23, 2011, which is the continuation of the present application, 164 pgs.

"Final Office Action", Office action response submitted Oct. 16, 2013, for U.S. Appl. No. 13/242,837—8 pages.

"Final Office Action", for U.S. Appl. No. 13/242,837, mailed Jul. 16, 2013 (9 pages).

Jennings, A. G. et al., "Chronic rupture of tendo Achillis", The Journal of Bone and Joint Surgery, vol. 84-B, No. 3, Apr. 2002, 361-363.

File History of U.S. Appl. No. 13/242,837, filed Sep. 23, 2011, which is the continuation of the present application, 129 pgs.

Partial File History of related U.S. Appl. No. 12/349,312, filed Jan. 6, 2009, 211 pgs.

\* cited by examiner

BEADED WOUND SPACER DEVICE

PRIORITY

This application claims priority to U.S. Provisional Application Ser. Nos. 60/806,727, filed Jul. 7, 2006; 60/827,595, filed Sep. 29, 2006; 60/863,572, filed Oct. 30, 2006; 60/870,092, filed Dec. 14, 2006 and 60/889,534, filed Feb. 12, 2007; the content of which are herein incorporated by reference.

BACKGROUND OF THE INVENTION

In high velocity wounds, such as those caused by explosive ordnance or explosive devices, significant tissue loss and tissue contamination is often experienced. Typical current field practice for war wounds and similar civilian trauma is to conduct meticulous debridement and serial irrigation of the wound, leaving the entire wound bed open, followed by application of high systemic concentrations of broad spectrum antibiotics and rapid evacuation of the patient to higher levels of care.

Furthermore, Iodoform gauze packing material has long been used to maintain wounds in an open status by packing the gauze into the wound bed. Such gauze packing material is the current standard, except for various exudate-absorbing or blood-absorbing wound dressing products, some of which include antimicrobial agents.

Another alternative wound packing material is manufactured by Biomet Europe under the trade name Septopal, and comprises chains of polymeric beads, positioned along a relatively stiff metal wire, the beads impregnated throughout with an antibiotic material. The distribution of antibiotic throughout Septopal-like beads usually results in incomplete and lengthy elution of the antibiotic, thereby causing unpredictable quantities of antibiotic to go unreleased. Also, such devices introduce the potential for prolonged low-level antibiotic elution from within the polymeric beads, and this prolonged low-level elution has the potential to promote development of drug-resistant bacteria.

Current medical literature also discusses the incorporation of antibiotic compositions throughout polymeric beads, and describes various methods of formation of such beads. For example, antibiotic composition can be mixed with polymethylmethacrylate and formed by hand or through a mold. Indeed, the Defense Medical Standardization Board (DMSB) treatment protocol for open wounds requires: "A minimum of 75 percent of all open wounds, with or without joint involvement, need to be treated with antibiotic beads. Pre-made antibiotic beads are not allowed by the FDA at this time, so will be made by the physician by using bone cement mixed with either a powder form of Vancomycin and/or Tobramycin." The release of the antibiotic in such devices can be quite variable and unpredictable, and appears dependent on the antibiotic concentration within the bead, the cracks, channels and pores formed in the final product, the manufacturing source of the bead substance, etc. This can result in unpredictable elution profiles, resulting in over dosing or under dosing of antibiotic compositions. Over dosing can result in systematic levels of antibiotic being inadvertently, and potentially detrimentally, administered. Under dosing can result in insufficient application of the antibiotic to the wound site, thereby failing to optimally control the growth of pathogens.

Therefore, a need exists for improved methods and materials for treating high velocity wounds, including methods and materials that allow for easy application and removal of packing material, that can be added quickly and in a sterile manner to a wound, that aid in limiting infections of the wound, that allow controlled release of active agents, and that help in the prevention of drug-resistant microbes.

SUMMARY OF THE INVENTION

The present invention is directed to a wound spacer device comprising multiple beads connected by non-absorbable suture material. The device is configured for placement in a wound bed, and is typically delivered from a surgical peel pack as an immediate yet generally temporary spacer to maintain the wound in an open condition. The device can be applied, for example, by a first responder to an injured individual, or can be applied by a trauma treatment facility, such as a Level 2 medical unit. In typical embodiments the device allows for site-specific controlled elution of an antimicrobial agent, such as Tobramycin, including defined elution over a period of time, such as 48 or 72 hours.

The device of the invention typically allows gas (air) permeation spacing beneath any temporary occlusive wrap (i.e. gauze) placed over the device and wounds. The beads and suture components of the device are easily and fully removable as an integrated unit prior to any surgical revision of the wound. The method and materials of the invention allow a particularly strong bond to be formed between the beads and the suture components, thereby providing improved handling of the device and superior ability to remove the device with lowered risk of having beads inadvertently break off or slide off the suture material. Typically the suture material and beads are bounded together so strongly that the suture material will break before the beads will slide off the suture material.

During a medical cycle of first response through hospitalization, the device may be replaced with a new device after wound lavage or other treatment but prior to final closure of a wound. Due to vascular damage, bone damage, and deep tissue contamination of high velocity wounds, the beads of the device (including the beads and typically the connecting components) are formed with materials that are lightweight, durable for the desired time span, and possess an antimicrobial active agent to mitigate wound related infections.

The device of the invention is particularly beneficial to treatment of wounds during transportation (such as evacuation of patients with blast injuries from a war zone). Such wounds are often tightly wrapped during transit in order to prevent fluids from leaking out of the wound, but such tight wrapping can create a functionally closed wound that is substantially hypoxic for an extended period of time (often 18 hours or more). These wounds can be a breeding ground for pathogens, and as such the device of the invention serves a critical need in preventing deterioration of the wound by preventing growth of pathogens and subsequent degradation of surrounding tissue. In this regard, the device limits damage to tissue at the zone of transition between the original wound bed and healthy tissue. Elimination or slowing of injury to the tissue in the zone of transition is critical because loss of tissue interferes with recovery and rehabilitation of the wound area and the patient overall.

The device is particularly useful in controlling aggressive pathogens, and can be tailored with specific elution profiles and active ingredients to treat endemic pathogens from various locations around the world. One primary mode of action of the device is to give a medical professional a mechanism to stabilize the wound bed and maintain the wound bed in an open condition. A secondary mode of action is to permit an occlusive dressing to be applied to the wound while maintaining some separation between much of the tissue and the dressing. This mode enables adequate gas permeation and exudate flow to optimize natural anti-infective and healing processes during the early trauma stage. A third mode of action is pharmacologic. This mode applies localized controlled release of an antibiotic as possible adjuvant therapy to parenteral administration so preventing the device from becoming a host for infections.

The beads of the device are desirably made of a core of a medical grade polymer, such as polyamide or polymethyl methacrylate (pMMA). Alternative medical grade materials, including various polymeric and non-polymeric materials, are also suitable for use with the invention. In most embodiments a shell covers the core, and is generally made of a medical grade polymer or polymer blend. Typically the shell is composed of more than one layer, with varying ingredients between the different layers.

The shell can be made to elute a pharmaceutically-active (or bioactive) agent, such as an aminoglycoside antibiotic, for example, tobramycin or gentamicin. Tobramycin is particularly well suited, relative to gentamicin, for its superior activity against *Pseudomonas aeruginosa* and *Acinetobacter baumannii*. The polymer or polymer blend used to form the shell generally controls the release of the active agent to produce local tissue concentrations of an active agent within acceptable clinical limits for a prescribed period of time (such as, for example, 24, 36, 48, 60, 72, 96, or 120 hours). Optionally, there is a change in elution rate to minimize residual fluid concentrations of antibiotic which are below their effective concentrations past the desired time of effect (thereby decreasing the probability of developing drug-resistant microbes).

In certain embodiments the shell comprises a bioactive agent in combination with one or more polymers, such as a first polymer component and a second polymer component. Suitable bioactive agents include, for example, tobramycin, vancomycin, amikacin, gentamicin, kanamycin, neomycin, netilmicin, paromomycin, streptomycin, and apramycin. In certain implementations, the shell composition comprises tobramycin having an elution profile such that the majority of the tobramycin elutes within 72 hours. In other implementations, the active agent is a combination of tobramycin and vancomycin having a 72 hour elution profile. Such short elution profiles are particularly useful for implementations in which a wound is left open and the wound spacer device will be removed within a few days of placement, typically to be replaced with a new wound spacer device.

In yet other implementations the wound spacer device is designed for longer placement in a wound. For example, in certain embodiments the wound spacer device includes an outer shell composition having a combination of tobramycin and vancomycin configured to have a multi-week elution profile, such as two, three, four, five, six, or more weeks. In one desirable implementation, the wound spacer has a four week (28 day) elution profile.

Alternatively, the wound spacer device may contain a degradable coating, such that the wound spacer device may be combined with an uncoated prosthesis at the time of implantation.

In certain implementations of the invention it is desirable to provide an intermediate tie-layer between the core of the bead and the coating. Such intermediate tie-layers can function to isolate the core of the bead from the coating, thereby limiting the flow of material either into or out of the core. In some implementations the intermediate layer effectively seals the bead core, preventing material from within the bead core from leaching out of the core. For example, if the bead core is formed with a solvent such as formaldehyde, then any residual formaldehyde can desirably be sealed into the bead by coating the bead with a substantially impenetrable layer. The tie layer can also provide an enhanced bond between the core and any subsequent layers applied over the top of the tie layer.

The polymer components forming the shell composition are typically adapted to be mixed or layered to provide a composition that exhibits an improved combination of physical characteristics (e.g., adherence, durability, etc.) and bioactive release characteristics as compared to the polymers when used alone or in admixture with other polymers previously known. In a desired embodiment the composition comprises at least one poly(alkyl)(meth)acrylate, poly(aryl)(meth)acrylate or poly(alkylaryl)(meth)acrylate as a first polymeric component and poly(ethylene-co-vinyl acetate) as a second polymeric component.

In a further example implementation, the bead substrate comprises polyamide, optionally with barium sulfate ($BaSO_4$) impregnated in the polyamide to improve imaging. The beads are overmolded onto a polyamide suture material. Preferably this polyamide suture material is substantially free of silicone to provide improved bond formation between the beads and the suture material. The bead substrate and suture material are coated with a basecoat containing tobramycin and photo-poly[vinylpyrrolidone]. In some embodiments the ratio of tobramycin to photo-poly[vinylpyrrolidone] is about 1:1. However, in other implementations this ratio is between about 1.5:1 to about 1:1.5; while in yet other implementations this ratio is between about 2:1 to 1:2; and in further implementations this ratio is between about 3:1 to 1:3. This mixture of tobramycin and photo-poly[vinylpyrrolidone] dissolved in a suitable solvent such as a solution of 50 percent water and 50 percent isopropanol at a loading concentration of 100 mg/ml of the tobramycin and photo-poly[vinylpyrrolidone]. In other implementations, different solvents (such as different alcohols) can be used, as well as different percentages of the solvent ingredients. For example, the solution can contain in some embodiments from 25 to 95 percent water and from 75 to 5 percent of isopropanol, other alcohols, other solvents, or mixtures thereof.

The coated beads and suture material containing the tobramycin and photo-poly[vinylpyrrolidone] mixture are typically allowed to dry for greater than one hour at ambient conditions, and then subjected to UV cure for three minutes. The objective in certain embodiments is to have a tobramycin drug load of approximately 1.0 to 1.5 mg per bead. In other implementations the objective is to have the tobramycin drug load of approximately 0.5 to 2.0 mg per bead; in other implementations the objective is to have the drug load of less than 1.5 mg per bead, while in other implementations the objective is to have the drug load of greater than 1.0 mg per bead.

After the base coat containing the tobramycin and photo-poly[vinylpyrrolidone] is applied, a middle coat formed using a combination of poly(butylmethacrylate) ("pBMA") and poly(ethylene-co-vinyl acetate) ("pEVA") is created to control elution of the tobramycin. The pBMA and pEVA layer is typically applied along with a photoreagent, such as tetrakis (4-benzophenylmethoxymethyl)methane along with a photo-poly[vinylpyrrolidone]. Typically these ingredients are added in chloroform. In one example embodiment, 5 parts pBMA to 95 parts pEVA to 5 parts photoreagent TETRAKIS(4-BENZOPHENYLMETHOXYMETHYL)METHANE to 15 parts photo-poly[vinylpyrrolidone] are added at a concentration of 115 mg/mL in chloroform. This coating is dried for greater than 5 minutes at ambient conditions, and then UV cured. In other implementations these ingredient concentrations are varied to obtain preferred elution properties.

In some implementations one or more layers on the device, optionally including a layer containing a bioactive agent, includes an acrylate but not PEVA, with a combined solubility parameter to enable proper drug release, for example as shown and disclosed in co-pending SurModics U.S. patent application Ser. No. 11/123,835, which is incorporated by reference in its entirety.

In certain implementations, after application of the pBMA/pEVA layer, a top coat of pBMA is applied at a concentration of 75 mg/mL in isopropanol. The top coat was dried for greater than 30 minutes at ambient conditions. An optional further overcoat can be added to reduce adhesion between beads and to the wound, said overcoat comprising (for example) photo-poly[vinylpyrrolidone].

In certain implementations the bioactive agent comprises tobramycin having an elution profile such that at least 80 percent of the tobramycin elutes within 100 hours of placement within a wound; in certain implementations the bioactive agent has an elution profile such that at least 50 percent of the tobramycin elutes within 100 hours of placement within a wound; in certain implementations the bioactive agent has an elution profile such that at least 20 percent of the tobramycin elutes within 8 hours of placement within a wound; in certain implementations the bioactive agent has an elution profile such that at least 50 percent of the tobramycin elutes within 48 hours of placement within a wound.

The above summary of the present invention is not intended to describe each discussed embodiment of the present invention. This is the purpose of the figures and the detailed description that follows.

BRIEF DESCRIPTION OF THE DRAWINGS

The invention may be more completely understood in consideration of the following detailed description of various embodiments of the invention in connection with the accompanying drawings, in which.

While the invention is susceptible to various modifications and alternative forms, specifics thereof have been shown by way of example and drawings, and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION

The present invention is directed, in part, to a temporary wound spacer device comprising multiple beads connected by non-absorbable flexible material. The device is configured for placement in a wound bed, is typically delivered from a surgical peel pack. The device is administered as an immediate yet temporary spacer to maintain the wound in an open condition while also allowing gas permeation spacing beneath any temporary occlusive wrap (i.e., gauze) placed over the device by the first medical responder. The beads and suture components of the device are easily and fully removed as an integrated unit prior to irrigation and debridement. During the medical evacuation process the device may be replaced repeatedly with a new device after wound lavage or other treatment but prior to final closure.

The device is well suited for combat injuries, including high velocity wounds, wounds with a high risk of infection, and wounds requiring delayed closure. The device is also well suited to many civilian medical applications, including dirty trauma wounds, revision surgeries, decubiticus ulcers, and for pre-closure wound care management. Due to the vascular damage and deep tissue contamination of these wounds, the beads of the device are formed with materials that are lightweight yet durable, and possess an antimicrobial material to mitigate device- and wound-related infections.

Figure 1:
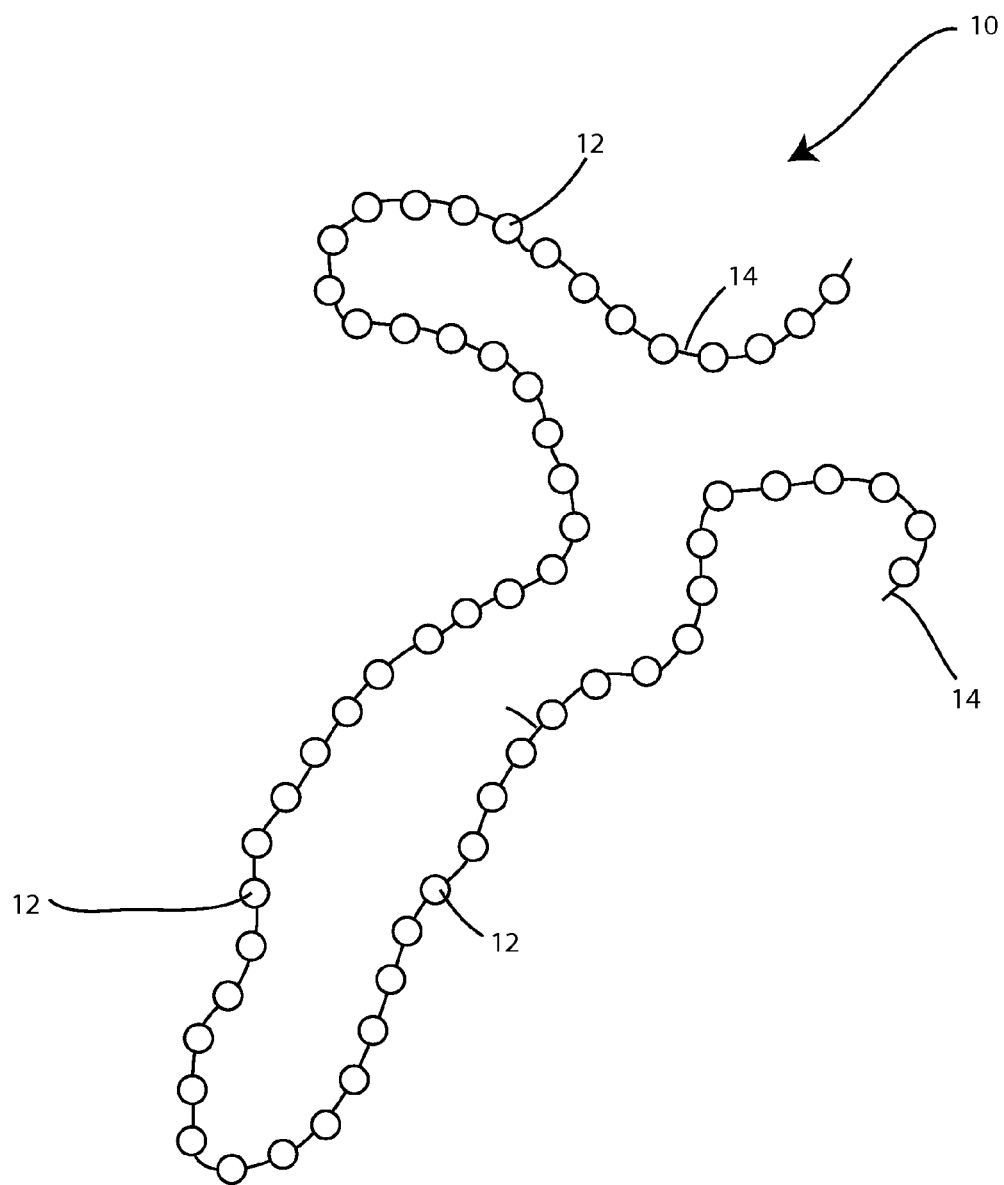
FIG. 1 shows a first wound spacer beaded device made in accordance with an implementation of the invention, the device comprising sixty beads
Figure 2A:
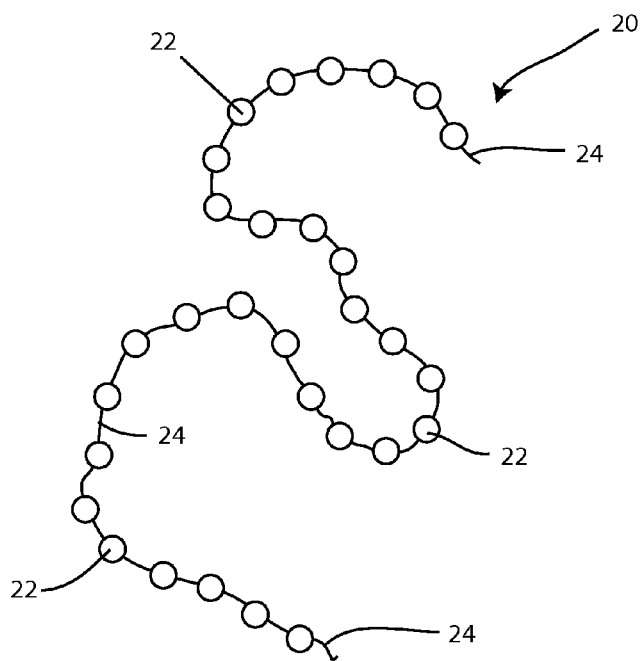
FIG. 2A shows a second wound spacer beaded device made in accordance with an implementation of the invention, the device comprising thirty beads.
Figure 2B:
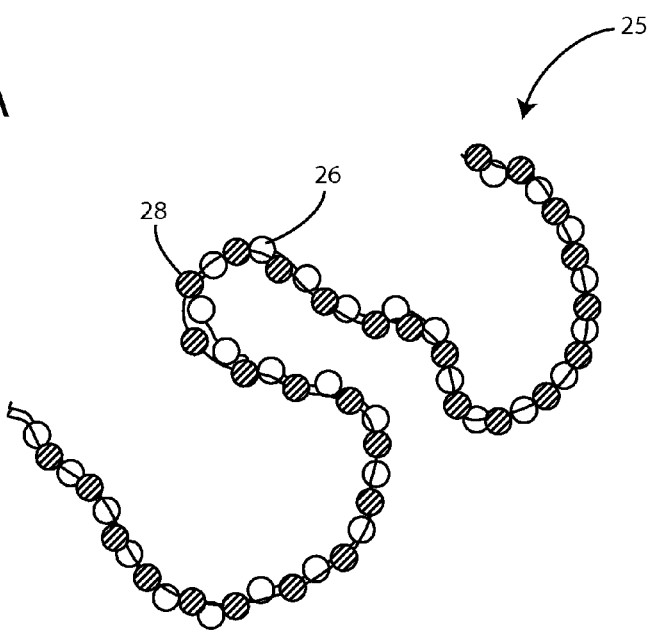
FIG. 2B shows a pair of wound spacer beaded devices (containing different active agents) made in accordance with an implementation of the invention, the devices each comprising thirty beads and the two devices twisted together in advance of placement in a wound bed.

The devices of the present invention can be constructed in numerous configurations, including various bead numbers, shapes, sizes, spacing of beads, core materials, and bead coatings or shells. In an example embodiment, shown in FIG. 1, a beaded device 10 made in accordance with an implementation of the invention contains sixty substantially spherical beads 12 positioned along a linking material 14. In an alternative embodiment, shown in FIG. 2A, a second beaded device 20 made in accordance with an implementation of the invention contains thirty substantially spherical beads 22 connected by linking material 24. In yet another alternative embodiment, shown in FIG. 2B, a pair of beaded devices 26, 28 is shown intertwined to form a combined device 25. Each of the beaded devices 26, 28 can contain different active agents in its beads, so that treatment can be tailored to a specific injury, a specific pathogen, etc. Typically the beaded devices 26, 28 of FIG. 2B would not be packaged together, but would be an optional way of administering a combination of two or more bead strands, typically having different active ingredients between the bead strands. However, alternative embodiments with more or fewer beads are also possible.

Thus, devices with less than twenty-five beads and more than fifty beads are appropriate for certain implementations, as are devices including twenty-five through fifty beads. In some implementations the devices will have one hundred beads or approximately one hundred beads. The beads are delivered in a sterile blister package in some implementations, or other sterile delivery device. The beads in each pack may be provided as a single strand or multiple strands. For example, a sterile blister pack containing one hundred beads can comprise two chains of fifty beads each.

The beads can have, for example, shapes ranging from oblong to substantially spherical. The minor axis in other than spherical shape is generally at least 1 mm, more generally at least 2 mm. The beads are typically less than 15 mm in diameter, and generally at least 3 mm in diameter. In some implementations the beads are between 5 and 10 mm in diameter, and in certain implementations from about 6 to 8 mm in diameter. In a specific embodiment the beads are approximately 7 mm in diameter.

The beads typically remain intact (non-deformable) in a wound area for 2 or more days and are substantially non-porous. In certain embodiments the beads are spaced at least 2 mm apart, more typically at least 3 mm apart, and frequently 5 mm apart or more. In general the beads are less than 15 mm apart, desirably less than 10 mm apart, and often less than 8 mm. In one embodiment the beads are spaced 5 mm apart, while in an alternative embodiment the beads are spaced 7 mm apart.

It is often desirable, for example, to have the beads be spaced apart by a distance of approximately one bead diameter, so that the bead chain can be completely reversed in direction between two beads. Such spacing allows the beads to conform more precisely to an irregularly shaped wound, and also allows the beads to be tightly placed within a packaging container.

The beads can have, for example, a volume greater than about 0.1 cubic centimeters per bead, alternatively a volume of about 0.25 cubic centimeters per bead, and still alternatively a volume of about 0.5 cubic centimeters per bead. In certain embodiments the volume of each bead of the device is greater than 0.1 cubic centimeters, and less than 0.3 cubic centimeters. In some implementations the volume of each bead is about 0.18 cubic centimeters. Thus, for example, in some embodiments the total volume of the device, based upon a volume per bead of 0.18 cubic centimeters, is about 5.4 cubic centimeters for a 30 bead device, about 10.8 cubic centimeters for a 60 bead device, and about 18 cubic centimeters for a 100 bead device. In alternative embodiments the devices have a total volume of approximately 25 cubic centimeters or more, and in some embodiments approximately 50 cubic centimeters. It will be noted that in general a device of the invention will fill a wound having a volume greater than the actual volume of the device, since the beads will also retain spaces between them when placed in a patient. These spaces allow exudates to leave the wound, and airflow into the wound. On especially large wounds it is possible to use two or more devices.

The linking material 14, 24 (of FIGS. 1 and 2A) is optionally constructed so as to be cut with a scalpel or other sharp device, so that the device may be shortened as appropriate to fill a specific wound. Suitable linking material includes, for example, braided polyamide suture material. In particular, polyamide suture material that is free of silicone is particularly desirable. The linking material should have a tensile strength to withstand the processing conditions that form the beads. The beads are held in place on the linking material such that there is no movement of the beads along the length of the linking material. The linking material 14, 24 also is optionally coated with a composition containing an antimicrobial active agent, so as to prevent the linking material from becoming a substrate for the growth of microbes. In most implementations the linking material will contain the same coating material as is present on the beads themselves, often multiple layers as present on the beads.

As described above, the beads can be made of a core of a medical grade polymer, such as polyamide or poly(methyl methacrylate) (pMMA). In certain embodiments the beads are composed of a core of polyamide, along with a shell containing tobramycin and one or more layers of polymeric materials, typically including UV-cured polymeric materials. The shell typically covers the core, and is made of a medical grade polymer or polymer blend. In most embodiments this shell contains two or more layers, the layers designed to provide appropriate properties for binding to the core, for holding the active agent, for controlling elution of the active agent, and for provide proper handling and storage properties. These various layers often include a blend of poly(butyl-methacrylate) (pBMA) and poly(ethylene-co-vinyl acetate) co-polymers (pEVA) for at least one layer, and often also include one or more layers containing photo-poly(vinylpyrrolidone).

As noted above, in certain embodiments, the shell (typically containing more than one layer) is made to control the release of a widely used aminoglycoside antibiotic, such as tobramycin, vancomycin, amikacin, gentamicin, kanamycin, neomycin, netilmicin, paromomycin, streptomycin, and apramycin. Other bioactive agents include, for example, various modified antimicrobials, and cationic steroidal antibiotics.

Additional suitable active agents include, for example, antimicrobial peptides taught in U.S. Pat. No. 5,714,577 (Antimicrobial Peptides); U.S. Pat. No. 5,945,507 (Antimicrobial Peptides); U.S. Pat. No. 6,835,713 (Virus Derived Antimicrobial Peptides); and U.S. Pat. No. 6,887,847 (Virus Derived Antimicrobial Peptides), all of which are incorporated by reference in their entirety. It is desirable, in certain embodiments, to use active agents that can disrupt the inner components and outer cell walls of potential infectious microbes.

In some embodiments all the beads of the device and the linking material joining the beads are coated with a composition containing the same active agent. However, in other implementations, different active agents are used on different beads, or different portions of each bead, or on the linking material. Thus, for example, two different active agents can be used on alternating beads. Such implementations can be appropriate, for example, when the two active agents are not compatible when applied together, yet have a complementary antimicrobial property, or when the two active agents need different delivery matrices.

In certain implementations, the shell composition comprises tobramycin having an elution profile such that the majority of the tobramycin has eluted within 72 hours. In yet other implementations the wound spacer device is designed for longer placement in a wound. For example, in certain embodiments the wound spacer device includes a shell having a combination of tobramycin and vancomycin configured to have a multi-week elution profile, such as two, three, four, five, six, or more weeks. In one desirable implementation, the wound spacer has a four week (28 day) elution profile.

Alternatively, the wound spacer device may contain a degradable coating, such that the wound spacer device may be combined with an uncoated prosthesis at the time of implantation. Such devices can be constructed such that they are fully biodegradable.

Figure 3A:
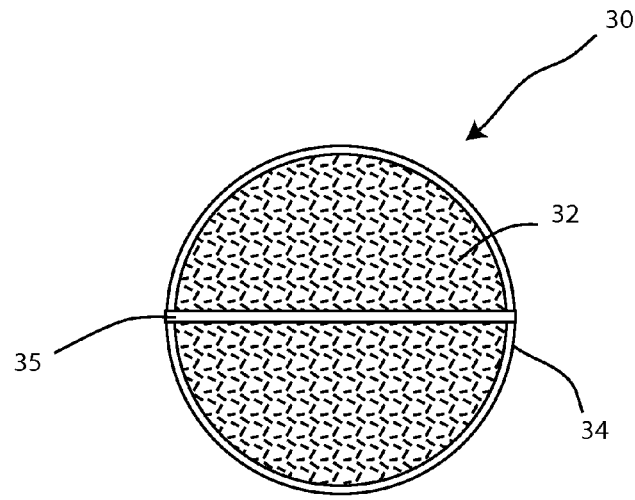
FIG. 3A shows a cross section of a first wound spacer bead made in accordance with an implementation of the invention.
Figure 3B:
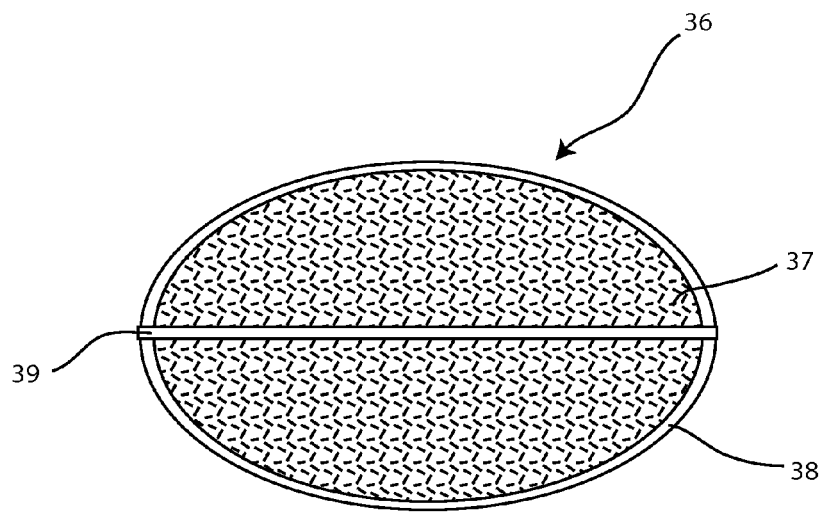
FIG. 3B shows a cross section of a second wound spacer bead made in accordance with an implementation of the invention.

Referring now to FIGS. 3A and 3B, two alternative configurations for beads made in accordance with the invention are shown in cross section. In FIG. 3A, a bead 30 is substantially spherical, containing a core 32 of first polymeric material and a shell 34. As described below, the shell 34 can be formed of various different polymeric materials and blends, and contains a bioactive agent, such as an antimicrobial or antibiotic agent. The bead 30 also shows a central path 35 through which a linking material (not shown) is placed. Generally the linking material runs through the center or diameter of the bead 30. The bead 30 is typically permanently affixed to the linking material in central path 35, such as by injection molding of the core 32 over pre-formed and pre-positioned linking material. In the alternative shown in FIG. 3B, the bead 36 is substantially oblong, but still contains a core 37 and a shell 38, along with a central path 39 for the linking material.

Figure 4A:
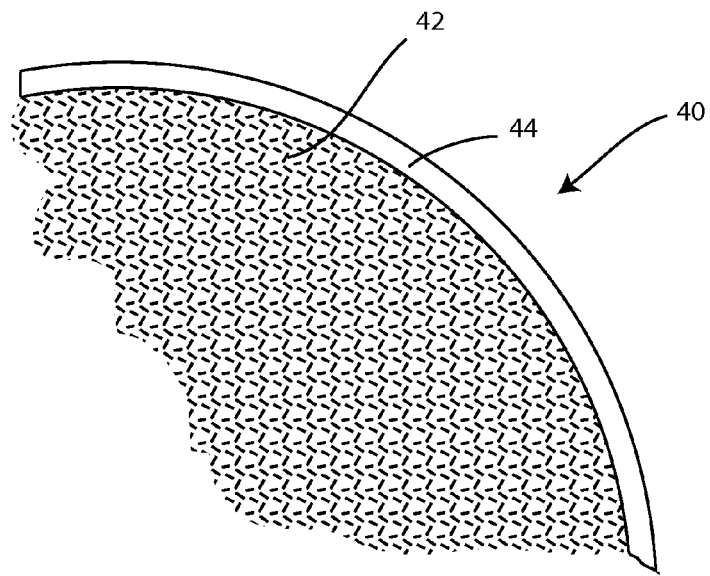
FIG. 4A shows a partial cross section of a wound spacer bead made in accordance with an implementation of the invention.
Figure 4B:
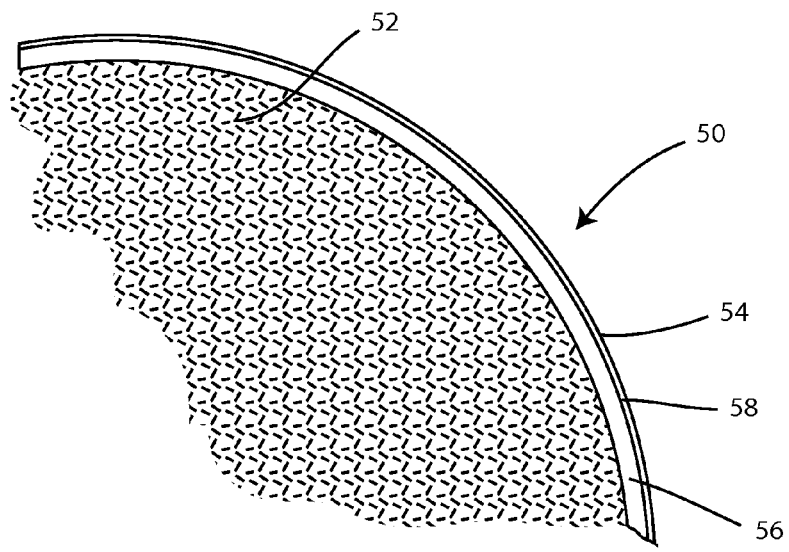
FIG. 4B shows a partial cross section of a wound spacer bead made in accordance with an implementation of the invention.

In reference now to FIGS. 4A and 4B, partial cross sections of beads 40 and 50 are shown, each of the beads made in accordance with an implementation of the invention. In FIG. 4A, bead 40 is shown with core 42 and a shell 44. The core 42 is a polymeric material, such as polymethyl methacrylate (pMMA). Other suitable core materials include, for example, polyamide, polypropylene, polyethylene, or other polymeric material. It will be appreciated, however, that in certain embodiments it is possible to make the core out of a non-polymeric material. For example, ceramics and metals are both suitable in certain embodiments.

In general, polymeric materials are preferred because of ease of manufacture and cost. Polymeric materials can be produced in multiple shapes and sizes, and do not require difficult firing, casting, or machining steps, as would typically be necessary for a ceramic or metal core. Desirable core materials will typically have good acid resistance, are abrasion resistant, alkali resistant, have high heat resistance and chemical resistance, and also are generally resistant to hydrocarbons. Desirable cores also typically have good impact resistance and are solvent resistant. Although less critical, UV resistance can be useful, especially if a UV-curable coating is used.

In some implementations the core 42 comprises polyamide. Suitable polyamides include poly(undecylamide) (e.g., Rilsan® BMNO MED from Arkema) and poly(hexamethyleneadipamide) (e.g., Zytel® 101 from Du Pont), which have good resistance to impact, abrasion, heat, acids, alkalis, hydrocarbons, and solvents. Various other polyamide materials can also be used. In some implementations the polyamide core (or other core material) is very smooth, while in yet other implementations the polyamide core has been roughened. The smoothness or roughness of the core will sometimes be influenced by the type of topcoat used. When maximum durability of the coating is desired, it is often appropriate to use a rough or roughened core material.

The core 42 must have sufficient integrity to remain intact during processing, shipping, storing, and application. Also, critically, it is necessary that the core have adequate integrity to be removed from a patient without any of the beads coming detached from linking material. Not only should the beads preferably not split or crumble, but also should not readily be stripped from the end of the linking material. Thus, a particularly strong bond between the linking material and the core material is desirable. In certain embodiments the linking material will actually break under a tension load before the bond between the linking material and core material breaks.

Typically the shell or outer surface coating contains at least one drug eluting polymer for placement into trauma wound sites. An antimicrobial/antibiotic drug is placed in the shell polymer to be eluted. Preferred drugs include, for example, either tobramycin or gentamicin, or a combination thereof. In one embodiment the drug or bioactive agent may be eluted in a burst and then released at efficacious levels over at least 2 days. The device is then removed and discarded when the patient is in a stable surgical environment where final debridement and surgical care is commenced.

In other embodiments, the device is configured for longer term use, and has a longer elution profile. This version of the device is designed for wounds which have been surgically treated and closed, but which are identified for revision work to be done at the same site over time. For this indication, a non-degradable polymer with a longer term elution profile (e.g., about one week to about 6 months) may be desirable. Also, a smaller sized bead may be called for if bone and tissue voids have been filled during surgery.

In the alternative, as shown in FIG. 4B, the bead 50 contains a core 52 and a multilayer shell 54 having inner layer 56 and outer layer 58. In certain embodiments the outer layer 58 is configured to provide hardness and durability to the device. Suitable materials for the outer layer 58 include pBMA. The pBMA can be applied without a drug in outer layer 58, so as to provide protection to the inner layer 56, such as protection against changes in temperature, including elevated temperatures. Generally it is desirable to have the outer layer 58 in such embodiments withstand prolonged exposure to temperatures above 100° F., more desirably above 110° F., and even more desirably above 120° F. In some embodiments, such as where the device will be used in desert environments, it is desirable to have the outer layer 58 remain intact at temperatures above 130° F., including temperatures above 150° F. In such embodiments the beads should exhibit little or no tackiness or degradation of the outer layer 58, and should further not demonstrate significant degradation of any inner layer 56 containing an antimicrobial agent. This outer layer 58 can also serve to promote lubricity between the beads, by being selected to have a lower coefficient of friction than the inner layer 56.

Figure 5A:
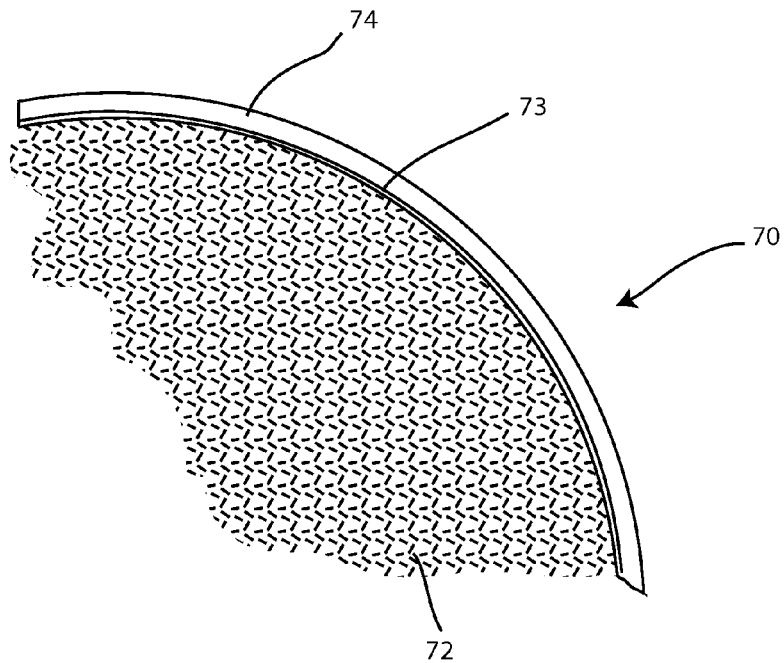
FIG. 5A shows a partial cross section of a wound spacer bead made in accordance with an implementation of the invention.
Figure 5B:
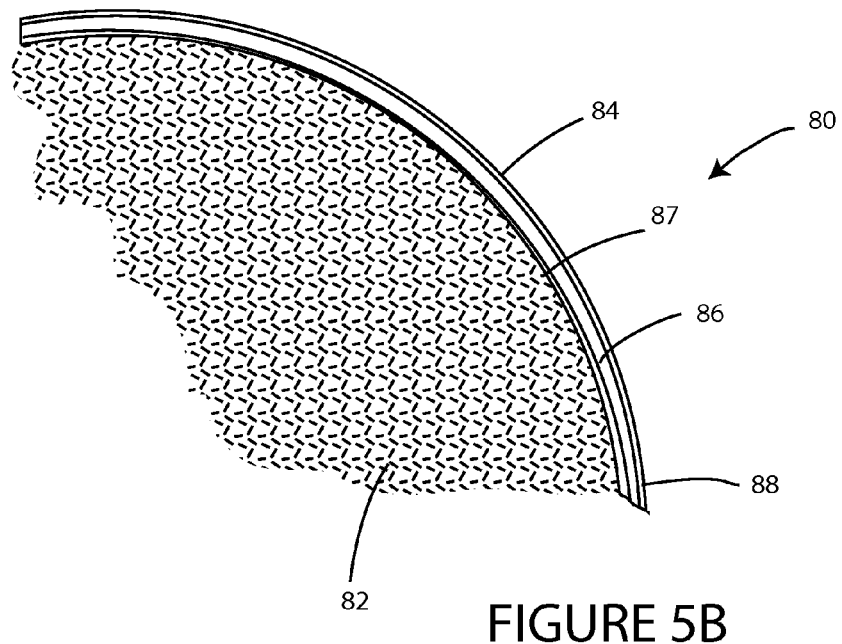
FIG. 5B shows a partial cross section of a wound spacer bead made in accordance with an implementation of the invention.

In reference now to FIGS. 5A and 5B, partial cross sections of beads 70 and 80 are shown, each of the beads made in accordance with an implementation of the invention. In FIG. 5A, bead 70 is shown with core 72 and a shell 74. The core 72 is a polymeric material, such as polymethyl methacrylate (pMMA). A tie-layer 73 is positioned between the core 72 and shell 74, and serves to prevent transfer of chemicals (solvents, active agents, etc.) between the core and shell, while also providing a good substrate to which the shell 74 can bind. Typically the shell or outer surface coating contains at least one drug eluting polymer for placement into trauma wound sites. An antimicrobial/antibiotic drug is placed in the shell polymer to be eluted. Preferred drugs include, for example, either tobramycin or gentamicin, or a combination thereof. In one embodiment the drug or bioactive agent may be eluted in a burst and then released at efficacious levels over at least 2 days. The device is then removed and discarded when the patient is in a stable surgical environment where final debridement and surgical care is commenced.

In the alternative, as shown in FIG. 5B, the bead 80 contains a core 82 and a multilayer shell 84 having interior layer 86 and outer layer 88, along with a tie-layer 87 positioned between the core 82 and the interior layer 86. In certain embodiments the outer layer 88 is configured to provide hardness and durability to the device. Suitable materials for the outer layer 88 include pBMA. The pBMA can be applied without a drug within outer layer 88, so as to provide protection to the interior layer 86, such as protection against changes in temperature, including elevated temperatures. Generally it is desirable to have the outer layer 88 in such embodiments withstand prolonged exposure to temperatures above 100° F., more desirably above 110° F., and even more desirably above 120° F. In some embodiments, such as where the device will be used in desert environments, it is desirable to have the outer layer 88 remain intact at temperatures above 130° F., including temperatures above 150° F.

In such embodiments the beads should exhibit little or no tackiness or degradation of the outer layer 88, and should further not demonstrate significant degradation of any inner layer 88 containing an antimicrobial agent. This outer layer 88 can also serve to promote lubricity between the beads.

Figure 6A:
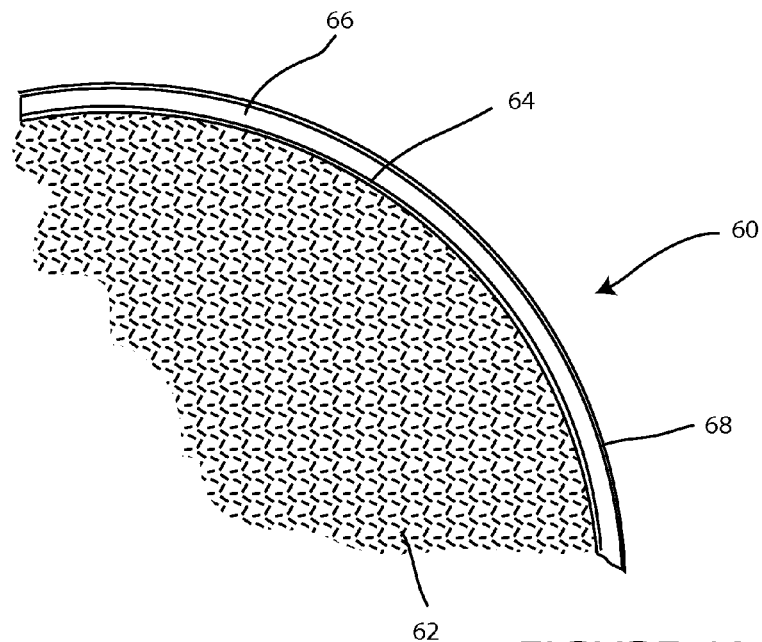
FIG. 6A shows a partial cross section of a wound spacer bead made in accordance with an implementation of the invention.

A further embodiment is shown in FIG. 6A, wherein a bead 60 contains a polyamide core 62. The core 62 optionally contains barium sulfate ($BaSO_4$) impregnated in the polyamide to improve imaging. The beads are overmolded onto a polyamide suture material (not shown). Preferably this polyamide suture material is substantially free of silicone to provide improved bond formation between the beads and the suture material. The bead core 62 is coated with a first layer 64 containing tobramycin and photo-poly[vinylpyrrolidone]. In some embodiments the ratio of tobramycin to photo-poly [vinylpyrrolidone] is about 1:1. However, in other implementations this ratio is between about 1.5:1 to about 1:1.5; while in yet other implementations this ratio is between about 2:1 to 1:2; and in further implementations this ratio is between about 3:1 to 1:3.

A second layer 66 formed using a combination of poly (butylmethacrylate) ("pBMA") and poly(ethylene-co-vinyl acetate) ("pEVA") is created to control elution of the tobramycin. The pBMA and pEVA layer is typically applied along with a photoreagent, such as tetrakis(4-benzophenyl-methoxymethyl)methane along with a photo-poly[vinylpyrrolidone]. Also, this pBMA and pEVA layer can optionally further include active agent within the layer, mixed with the pBMA and pEVA. In one example embodiment, 5 parts pBMA to 95 parts pEVA is used in this layer. A third layer comprising a top coat 68 of pBMA is applied in certain embodiments to further control elution and reduce adhesion between beads, and also to prevent adhesion to wound surfaces when placed within a patient.

Figure 6B:
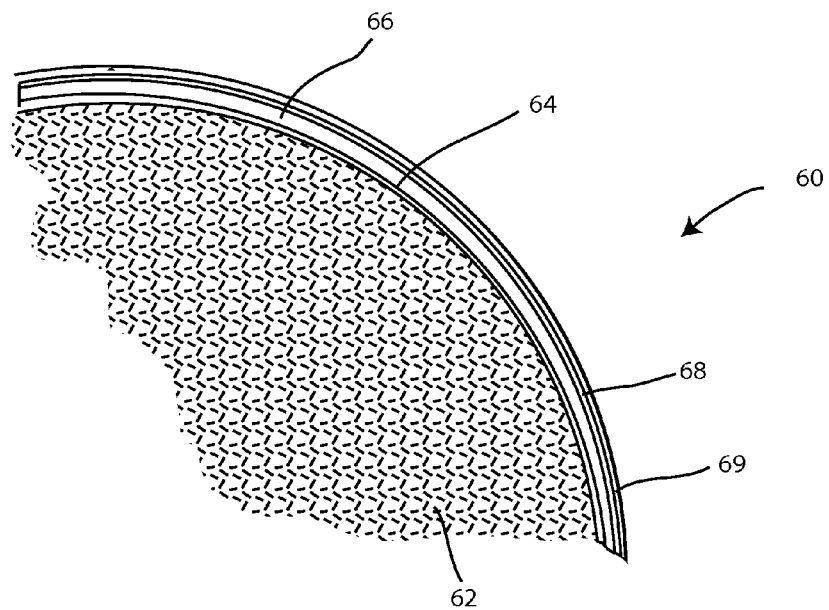
FIG. 6B shows a partial cross section of a wound spacer bead made in accordance with an implementation of the invention.

In reference now to FIG. 6B, a further alternative to FIG. 6A is shown, with an optional further overcoat 69 added over layer 68 to reduce adhesion between beads and to the wound. The overcoat 69 comprising (for example) photo-poly[vinylpyrrolidone].

In certain embodiments of the invention a degradable coating is applied to the device, the degradable coating typically containing one or more active agents. A hospital-based self contained modular coating system can be used. Such hospital-based systems can include a self contained modular coating system with modular loadable reagent and bioactive agent containers. Such systems optionally have a small footprint, are leak and explosion proof, and contain a post-coating sterilizing module.

A spray-on coating system using a syringe or nozzle spray applicator system can optionally be used, allowing highly modular canister type configurations. Such coating systems are suitable for redox and other techniques, and are adaptable to a range of molecular weight bioactive agents. In the alternative, the coating can be applied in a dense formulation for lipstick dispenser type of application. Such implementations have a high tenacity with substantial cohesion and adhesion of coating. The coating can be applied surgeon selectable sites for attachment to the device at the time of surgery and be pre-loaded with bioactive agent.

In an alternative embodiment, a coating and reservoir within the internal depot of the implant contains dispersal lumens controlled by natural switches responsive to adjacent tissue/serum condition. Such implementations allow a highly directional capability around the implant, with optional neutralization of any residual reservoir volume. Alternatively, an autologous wound coating system can include an enhanced protein, and is well suited to a high volume trauma or scheduled surgery market. Use of such autologous source enables rapid clinical acceptance, and can be combined with other pro-healing components. In the alternative, pre-formed thin films may be attached to the device at the time of surgery. Such thin films are useful for high surface tension attachment pre-loaded with bioactive agent, and are suitable for site selective applications.

Figure 7A:
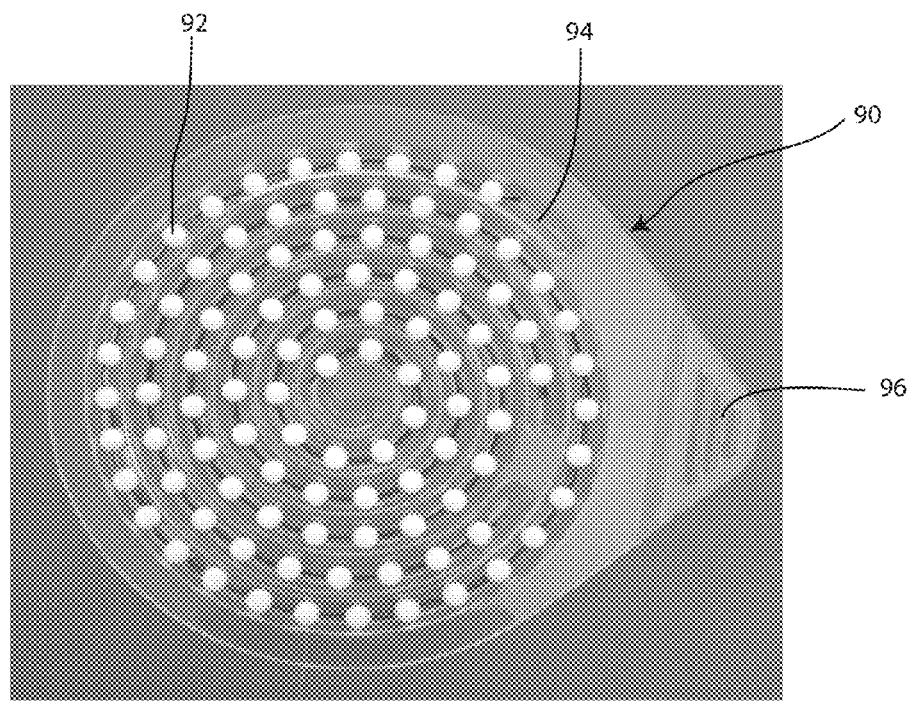
FIG. 7A shows a beaded wound spacer device in a sterile blister pack.
Figure 7B:
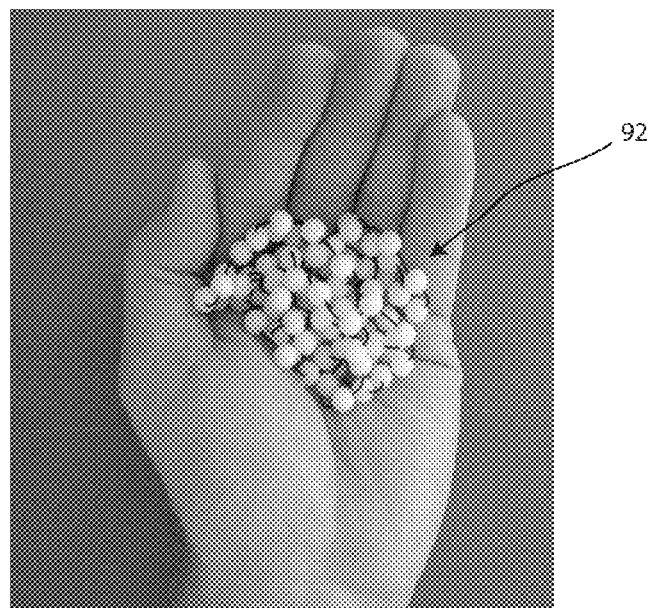
FIG. 7B shows a beaded wound spacer device in the palm of a hand, demonstrating flexibility of the device to conform to a contained space.

In reference now to FIGS. 7A and 7B, a beaded wound spacer device in a sterile blister pack and a beaded wound spacer device in the palm of a hand is depicted. In FIG. 7A, a blister pack 90 containing a channel 94 retains one or more beaded devices 92. The beaded device 92 is coiled within the blister pack 90. Typically a top layer film is removed at tab 96, exposing the sterile beaded device 92 so that it can be immediately administered to a patient. The beaded device 92 can be poured right into a wound opening, be lowered in as a strand, dropped in as a clump, etc. In reference now to FIG. 7B, the flexibility and ease of positioning of the beaded device 92 is shown, with the device 92 readily conforming to the palm of a hand.

It is desirable, in certain embodiments of the invention to reduce the active agent into small particles prior to incorporation into the inner shell of the bead coating. For example, the active agent can be wet milled in a ball mill in the presence of a liquid dispersant, such as chloroform. Suitable active agents for wet milling in chloroform include tobramycin.

As noted above, in certain implementations the beads contain an inner shell comprising a combination of the active agent and pEVA. In some implementations the ratio of active agent to pEVA is approximately 50/50. However, in other implementations of invention, the ratio of active agent to pEVA is from 25/75 to about 75/25, while in yet other implementations the ratio of active agent to pEVA is outside of these ranges.

In some example implementations the desired elution profile has a burst of drug for at least two hours, typically about four hours, but generally less than ten hours, at levels above 40 micrograms/milliliter of surrounding exudates, followed by a tapered release over an extended period of at least 50 hours, generally about 100 hours, and typically less than 200 hours for most drug to be released.

Devices made in accordance with the durable embodiment of the invention generally do not materially lose volume in a wound bed for up to 2 days, greater for other defined periods. Also, the devices generally remain intact during removal from a wound, and can be removed using any position on the device for handling, whether that position is a bead or the linking material.

Packaging of devices made in accordance with the invention typically utilizes a surgical peel pack design comprising a tray with a cover. Primary packaging may be configured as a minimum profile (palm sized) and incorporates minimum unused volume. In some implementations the packaging can be held in one hand while a second hand peels back the package cover and does not require hand contact with the device. In such implementations the device utilizes gravity deployment. Secondary packaging can contain multiple primary device packages. In the primary packaging, in certain embodiments, the beads do not contact one another. Packaging materials are selected such that they do not promote or permit significant degradation of drug, as statistically measured via drug content and potency test methods.

In yet another alternative embodiment, a permanently implantable version of the device is created for use in post-surgical settings prior to wound closure. Any wound which is at a higher than normal risk for infection is a candidate for use of this product. For example, high impact wounds caused on battlefields which may distribute infected agents into deep tissue, wounds in dirty environments such as farms and industrial settings, and wounds in immuno-compromised patients all present high infection risks. Such devices are preferably made of a degradable/resorbable polymers which enables elution of the drug in a pattern of desired amount in four days and the remainder over a period of an additional 5-6 weeks. The linking material is also selected as a suitable degradable suture or suture-like material designed for the specific degradation and elution profiles desired.

Another embodiment of wound spacer device would be seen in infected joint replacements. This embodiment has the controlled elution of antimicrobial agents from the device's shell where the core is formed in shape of desired joint spacer. Joint spacers for the knee, hip or any replaced joint are selected and placed in the infected space following removal of the prosthetic until the infection is gone. Such spacers are typically formed from PMMA and have antibiotic mixed throughout the spacer similar to traditional antibiotic beads. Likely, such spacers have the same limitations and concerns as traditional beads.

Antibiotics and other bioactive agents can be released from the surface of the device to minimize the possibility of infection. Another benefit to the local release of bioactive agents is the avoidance of toxic concentrations of such agents which are sometimes necessary, when given systemically, to achieve therapeutic concentrations at the site where they are needed. This is particularly important in wounds with compromised vasculature, therefore unable to receive effective concentrations throughout portions of the wound bed. In certain embodiments the outer shell composition comprises a bioactive agent in combination with a plurality of polymers, including a first polymer component and a second polymer component. The polymer components are adapted to be mixed to provide a mixture that exhibits an optimal combination of physical characteristics (e.g., adherence, durability, etc.) and bioactive release characteristics as compared to the polymers when used alone or in admixture with other polymers previously known. In a preferred embodiment the composition comprises at least one poly(alkylmethacrylate), as a first polymeric component and poly(ethylene-co-vinyl acetate) ("pEVA") as a second polymeric component.

The shells of the beads of the device typically comprise a polymer system for delivery of a biologically active agent or agents. Suitable polymer systems include, without limitation, those described in U.S. Pat. No. 6,214,901 (Bioactive Agent Release Coating); U.S. Pat. No. 6,344,035 (Bioactive Agent Release Coating), U.S. Pat. No. 6,890,583 (Bioactive Agent Release Coating), U.S. Pat. No. 7,008,667 (Bioactive Agent Release Coating), U.S. Pat. No. 7,097,850 (Bioactive Agent Release Coating and Controlled Release Method); U.S. Patent Application No. 20060240072 (Crosslinkable Macromers); and U.S. Patent Application No. 20060030669 (Thermally-reactive polymers) all of which are incorporated by reference in their entireties. In one implementation, the polymer system comprises a crosslinkable macromer system that includes two or more polymer-pendent polymerizable groups and one or more polymer-pendent initiator groups. The polymerizable groups and the initiator group(s) can be pendent on the same or different polymeric backbones. The macromer system provides advantages over the use of polymerizable macromers and separate, low molecular weight initiators, including advantages with respect to such properties as nontoxicity, efficiency, and solubility.

The composition and method can be used to control the amount and rate of bioactive agent (e.g., drug) release from one or more surfaces of a device. In a preferred embodiment, the method employs a mixture of hydrophobic polymers in combination with one or more bioactive agents, such as a pharmaceutical agent, such that the amount and rate of release of agent(s) from the device can be controlled, e.g., by adjusting the relative types and/or concentrations of polymers in the shell. For a given combination of polymers, for instance, this approach permits the release rate to be adjusted and controlled by simply adjusting the relative concentrations of the polymers in the coating mixture. This obviates the need to control the bioactive release rate by polymer selection, multiple coats, or layering of coats, and thus greatly simplifies the manufacture of devices. However, such layering or multiple coats may also be advantageous in order to achieve combinations, achieve asymmetric release profiles of an active agent or for physical protection of the device.

A desirable coating of this invention includes a mixture of two or more polymers having complementary physical characteristics, and a pharmaceutical agent or agents applied to the surface of the device. The applied coating is cured (e.g., solvent evaporated, exposed to UV light) to provide a tenacious bioactive-releasing coating on the surface of the beads and, optimally, the linking material. The complementary polymers are selected such that a broad range of relative polymer concentrations can be used without detrimentally affecting the desirable physical characteristics of the polymers. By use of the polymer mixtures of the invention the bioactive release rate from a wound spacer beaded device can be manipulated by adjusting the relative concentrations of the polymers. Similarly, a spectrum of pharmaceutical agents can be delivered from the coating without the need to find a new polymer or layering the coating on the device.

In order to provide a preferred bead shell layer, in one implementation, a composition is prepared to include a solvent, a combination of complementary polymers dissolved in the solvent, and the bioactive agent or agents dispersed in the polymer/solvent mixture. The solvent is preferably one in which the polymers form a true solution. The pharmaceutical agents may either be soluble in the solvent or form a suspension throughout the solvent. In certain embodiments the pharmaceutical agent can remain a solid suspended in the solution such that a gel or gel-like material is formed. For example, it is possible to wet-mill certain pharmaceutical agents (such as tobramycin) in a solvent that does not dissolve the pharmaceutical agent (such as chloroform) so as to produce reduced-size particles of pharmaceutical agent, the particles generally having a size distribution allowing easy formation of suspensions or gels. Also, in certain embodiments the active agent is milled in the presence of the polymer, such as pEVA. Wet-milling of the active agent and pEVA in certain embodiments creates a viscous-gel after approximately 4 to 8 hours. This gel demonstrates the interesting property that it returns to a fluid state upon shaking. Thus, the gel shows excellent handling properties but is readily applied as a coating by agitating the gel.

In certain implementations of the invention it is desirable to provide an intermediate tie-layer between the core of the bead and the coating. Such intermediate tie-layers can function to isolate the core of the bead from the coating, thereby limiting the flow of material either into or out of the core. In some implementations the intermediate layer effectively seals the bead core, preventing material from within the bead core from leaching out of the core. For example, if the bead core is formed with a solvent such as formaldehyde, then any residual formaldehyde can desirably be sealed into the bead by coating the bead with a substantially impenetrable layer.

For example, a parylene tie-layer coating composition (Parylene is a trademark of the Union Carbide Corporation) can be used between the bead core and the coating layer. Alternatively, a polymer or copolymer tie-layer can be used having, for example, a polyacrylamide backbone or a polyethylene oxide-based polymer or copolymer. One example of a photoreactive polymer comprises a copolymer of vinylpyrrolidone and N-[3-(4-Benzoylbenzamido)propyl]methacrylamide (BBA-APMA); another example is a copolymer of acrylamide and BBA-APMA.

In other embodiments, the device is configured for longer term use, and has a longer elution profile. This version of the device is designed for wounds which have been surgically treated and closed, but which are identified for revision work to be done at the same site over time. For this indication, a non-degradable polymer with a longer term elution profile (e.g., about one week to about 6 months) may be desirable. Also, a smaller sized bead may be called for if bone and tissue voids have been filled during surgery.

The resultant composition can be applied to the device in any suitable fashion, e.g., it can be applied directly to the surface of the device, or alternatively, to the surface of a surface-modified device, by dipping, spraying, or any conventional technique. Generally the shell forming composition is applied to both the beads and the linking material joining the beads. The method of applying the coating composition to the device is typically governed by the geometry of the device and other process considerations. The coating is subsequently cured by evaporation of the solvent. The curing process can be performed at room temperature, elevated temperature, or with the assistance of vacuum. The coating may also be cured by exposing the coating to UV light.

Various methods of applying the coating can be used. In some implementations the coating can be applied by dipping the device into one or more liquids containing monomers, polymers, solvents, and active ingredients. In some implementations the active ingredient will be added as a liquid to the coating, while in others the active ingredient is wet milled before adding to the coating. When multiple layers are used, the layers may form a blend of monomers and polymers extending between the layers.

The polymer mixture for the shell of the beads for use in this invention is preferably biocompatible, e.g., such that it results in little to no induction of inflammation or irritation when implanted. In addition, the polymer combination is generally useful under a broad spectrum of both absolute concentrations and relative concentrations of the polymers. This means that the physical characteristics of the coating, such as tenacity, durability, flexibility, and expandability, will typically be adequate over a broad range of polymer concentrations. Furthermore, the ability of the coating to control the release rates of a variety of pharmaceutical agents can preferably be manipulated by varying the absolute and relative concentrations of the polymers.

In one implementation a mixture of polymer compositions is used to form the shell. A first polymer component provides an optimal combination of various structural/functional properties, including hydrophobicity, durability, bioactive agent release characteristics, biocompatability, molecular weight, and availability (and cost). Examples of suitable first polymers include poly(alkylmethacrylates), and in particular, those with alkyl chain lengths from 2 to 8 carbons, and with molecular weights from 50 kilodaltons to 900 kilodaltons. An example of a particularly preferred first polymer is poly n-butylmethacrylate. Such polymers are available commercially, e.g., from Sigma-Aldrich of St. Louis, Mo., with molecular weights ranging from about 200,000 daltons to about 320,000 daltons, and with varying inherent viscosity, solubility, and form (e.g., as crystals or powder).

A second polymer component for the shell of such embodiments provides an optimal combination of similar properties, and particularly when used in admixture with the first polymer component. Examples of suitable second polymers are available commercially and include poly(ethylene-co-vinyl acetate) having vinyl acetate concentrations of between about 10% and about 50%, in the form of beads, pellets, granules, etc. (commercially available are 12%, 14%, 18%, 25%, 33%). pEVA co-polymers with lower percent vinyl acetate become increasingly insoluble in typical solvents, whereas those with higher percent vinyl acetate become decreasingly durable.

A particularly preferred polymer mixture includes mixtures of poly(butylmethacrylate) (pBMA) and poly(ethylene-co-vinyl acetate) co-polymers (pEVA). This mixture of polymers has proven useful with absolute polymer concentrations (i.e., the total combined concentrations of both polymers in the coating composition), of between about 0.25 and about 70 percent (by weight). It has furthermore proven effective with individual polymer concentrations in the coating solution of between about 0.05 and about 70 weight percent. In one preferred embodiment the polymer mixture includes poly(n-butylmethacrylate) (PBMA) with a molecular weight of from 100 kilodaltons to 900 kilodaltons and a pEVA copolymer with a vinyl acetate content of from 24 to 36 weight percent. In a particularly preferred embodiment the polymer mixture includes poly(n-butylmethacrylate) with a molecular weight of from 200 kilodaltons to 400 kilodaltons and a pEVA copolymer with a vinyl acetate content of from 30 to 34 weight percent. The concentration of the bioactive agent or agents dissolved or suspended in the coating mixture can range from 0.01 to 90 percent, by weight, based on the weight of the final coating composition.

The composition of the present invention used to form the shell of the beads and linking material can be used to coat a beaded device surface using any suitable means, e.g., by dipping, spraying and derivations thereof. The suitability of the coating composition for use on a particular material, and in turn, the suitability of the coated composition can be evaluated by those skilled in the art, given the present description. In turn, the coating thickness of a presently preferred composition will typically be in the range of about 5 micrometers to about 100 micrometers, often from about 7 to 10 micrometers. This level of coating thickness is generally required to provide an adequate density of drug to provide adequate activity under physiological conditions.

In an alternative embodiment, the present invention provides a crosslinkable macromer system comprising two or more polymer-pendent polymerizable groups and one or more polymer-pendent initiator groups. In a preferred embodiment, the polymerizable groups and the initiator group(s) are pendent on the same polymeric backbone. In an alternative preferred embodiment, the polymerizable groups and initiator group(s) are pendent on different polymeric backbones. In a further preferred embodiment, the polymerizable groups are present in small molecules mixed with the polymers.

In a first alternative embodiment, the macromer system comprises a polymeric backbone to which are covalently bonded both the polymerizable groups and initiator group(s). Pendent initiator groups can be provided by bonding the groups to the backbone at any suitable time, e.g., either prior to the formation of the macromer (for instance, to monomers used to prepare the macromer), or to the fully formed macromer itself. The macromer system itself will typically comprise only a small percentage of macromers bearing both initiator groups and polymerizable groups. The majority of macromers will provide only pendent polymerizable groups, since the initiator groups are typically sufficient if present at far less than 1:1 stoichiometric ratio with macromer molecules.

In an alternative embodiment, the macromer system comprises both polymerizable macromers, generally without pendent initiator groups, in combination with a polymeric initiator. In either embodiment, the initiator will be referred to herein as a "polymeric initiator", by virtue of the attachment of such initiator groups to a polymeric backbone. In an example embodiment, the pendent initiator groups are selected from the group consisting of long-wave ultra violet (LWUV) light-activatable molecules such as; 4-benzoylbenzoic acid, [(9-oxo-2-thioxanthanyl)-oxy]acetic acid, 2-hydroxy thioxanthone, and vinyloxymethylbenzoin methyl ether; visible light activatable molecules; eosin Y, rose bengal, camphorquinone and erythrosin, and thermally activatable molecules; 4,4' azobis(4-cyanopentanoic) acid and 2,2-azobis[2-(2 imidazolin-2-yl)propane]dihydrochloride. An important characteristic of the initiator group is the ability to be coupled to a preformed macromer containing polymerizable groups, or to be modified to form a monomer which can take part in the macromer synthesis, which is subsequently followed by the addition of polymerizable groups. In such an embodiment, the pendent polymerizable groups are preferably selected from the group consisting of pendent vinyl groups, acrylate groups, methacrylate groups, ethacrylate groups, 2-phenyl acrylate groups, acrylamide groups, methacrylamide groups, itaconate groups, and styrene groups.

In a further embodiment, the polymeric backbone for the device shell is selected from the group consisting of synthetic macromers, such as polyvinylpyrrolidone (pVP), polyethylene oxide (pEO), and polyethylene glycol (pEG); derivatizable naturally occurring polymers such as cellulose; polysaccharides, such as hyaluronic acid, dextran, and heparin; and proteins, such as collagen, gelatin, and albumin.

The polymeric backbone can be either synthetic or naturally-occurring, and includes a number of macromers previously described as useful for the preparation of polymeric matrices. Generally, the backbone is one that is soluble, or nearly soluble, in aqueous solutions such as water, or water with added organic solvent (e.g., dimethylsulfoxide) or can be rendered soluble using an appropriate solvent or combination of solvents. Alternatively, the polymeric backbone can be a material which is a liquid under ambient physiological conditions. Backbones for use in preparing biodegradable gels are preferably hydrolyzable under in vivo conditions.

As used herein, the term "polymerizable group" will generally refer to a group that is polymerizable by initiation by free radical generation, most preferably by photoinitiators activated by visible or long wavelength ultraviolet radiation. Preferred polymerizable groups include acrylates, methacrylates, ethacrylates, itaconates, acrylamides, methacrylamide, and styrene. Typically, polymerizable groups are incorporated into a macromer subsequent to the initial macromer formation using standard thermochemical reactions. Thus, for example, polymerizable groups can be added to collagen via reaction of amine containing lysine residues with acryloyl chloride or glycidyl acrylate. These reactions result in collagen containing pendent polymerizable moieties.

Similarly, when synthesizing a macromer for use as described in the present invention, monomers containing reactive groups can be incorporated into the synthetic scheme. For example, hydroxyethylmethacrylate (HEMA) or aminopropylmethacrylamide (APMA) can be copolymerized with N-vinylpyrrolidone or acrylamide yielding a water-soluble polymer with pendent hydroxyl or amine groups. These pendent groups can subsequently be reacted with acryloyl chloride or glycidyl acrylate to form water-soluble polymers with pendent polymerizable groups.

Suitable polymeric initiators include photosensitive molecules which capture light energy and initiate polymerization of the macromers. Other preferred polymeric initiators are thermosensitive molecules which capture thermal energy and initiate polymerization of the macromers. Photoinitiation of the free radical polymerization of macromers of the present invention will generally occur by one of three mechanisms. The first mechanism involves a homolytic alpha cleavage reaction between a carbonyl group and an adjacent carbon atom. This type of reaction is generally referred to as a Norrish type I reaction. Examples of molecules exhibiting Norrish type I reactivity and useful in a polymeric initiating system include derivatives of benzoin ether and acetophenone.

The second mechanism involves a hydrogen abstraction reaction, either intra- or intermolecular. This initiation system can be used without additional energy transfer acceptor molecules and utilizing nonspecific hydrogen abstraction, but is more commonly used with an energy transfer acceptor, typically a tertiary amine, which results in the formation of both aminoalkyl radicals and ketyl radicals. Examples of molecules exhibiting hydrogen abstraction reactivity and useful in a polymeric initiating system, include analogs of benzophenone, thioxanthone, and camphorquinone. When using a polymeric initiator of the hydrogen abstraction variety, pendent tertiary amine groups can be incorporated into the polymeric backbone of the macromer. This will insure that all free radicals formed are polymer-bound.

The third mechanism involves photosensitization reactions utilizing photoreducible or photo-oxidizable dyes. In most instances, photoreducible dyes are used in conjunction with a reductant, typically, a tertiary amine. The reductant intercepts the induced triplet producing the radical anion of the dye and the radical cation of the reductant. Examples of molecules exhibiting photosensitization reactivity and useful in a polymeric initiating system include eosin Y, rose bengal, and erythrosin. Reductants can be incorporated into the polymer backbone, thereby assuring that all free radicals will be polymer-bound.

Thermally reactive polymeric initiators are also useful for the polymerization of macromers to form the shell of the beads. Examples of thermally reactive initiators usable in a polymeric initiating system include 4,4' azobis(4-cyanopentanoic acid) and analogs of benzoyl peroxide. A surprisingly beneficial effect of the use of polymeric initiators to polymerize macromers is the increased efficiency of polymerization exhibited by these polymeric initiators as compared to their low molecular weight counterparts. This increased efficiency is seen in all three photoinitiation mechanisms useful for the polymerization of macromers.

Embodiments of the invention can include one or more non-degradable (durable) polymers. In an embodiment, the non-degradable polymer includes a plurality of polymers, including a first polymer and a second polymer. When the coating solution contains only one polymer, it can be either a first or second polymer as described herein. As used herein, term "(meth)acrylate" when used in describing polymers shall mean the form including the methyl group (methacrylate) or the form without the methyl group (acrylate).

First polymers of the invention can include a polymer selected from the group consisting of poly(alkyl(meth)acrylates) and poly(aromatic(meth)acrylates), where "(meth)" will be understood by those skilled in the art to include such molecules in either the acrylic and/or methacrylic form (corresponding to the acrylates and/or methacrylates, respectively). An exemplary first polymer is poly(n-butyl methacrylate) (pBMA). Such polymers are available commercially, e.g., from Aldrich, with molecular weights ranging from about 200,000 Daltons to about 320,000 Daltons, and with varying inherent viscosity, solubility, and form (e.g., as crystals or powder). In some embodiments, poly(n-butyl methacrylate) (PBMA) is used with a molecular weight of about 200,000 Daltons to about 300,000 Daltons.

Examples of suitable first polymers also include polymers selected from the group consisting of poly(aryl(meth)acrylates), poly(aralkyl(meth)acrylates), and poly(aryloxyalkyl (meth)acrylates). Such terms are used to describe polymeric structures wherein at least one carbon chain and at least one aromatic ring are combined with acrylic groups, typically esters, to provide a composition. In particular, exemplary polymeric structures include those with aryl groups having from 6 to 16 carbon atoms and with weight average molecular weights from about 50 to about 900 kilodaltons. Suitable poly(aralkyl(meth)acrylates), poly(arylalky(meth)acrylates) or poly(aryloxyalkyl (meth)acrylates) can be made from aromatic esters derived from alcohols also containing aromatic moieties. Examples of poly(aryl(meth)acrylates) include poly(9-anthracenyl methacrylate), poly(chlorophenylacrylate), poly(methacryloxy-2-hydroxybenzophenone), poly(methacryloxybenzotriazole), poly(naphthylacrylate) and -methacrylate), poly(4-nitrophenyl acrylate), poly(pentachloro(bromo, fluoro) acrylate) and -methacrylate), and poly(phenyl acrylate) and -methacrylate). Examples of poly(aralkyl(meth)acrylates) include poly(benzyl acrylate) and -methacrylate), poly(2-phenethyl acrylate) and -methacrylate, and poly(1-pyrenylmethyl methacrylate). Examples of poly(aryloxyalkyl (meth)acrylates) include poly(phenoxyethyl acrylate) and -methacrylate), and poly(polyethylene glycol phenyl ether acrylates) and -methacrylates with varying polyethylene glycol molecular weights.

Examples of suitable second polymers are available commercially and include poly(ethylene-co-vinyl acetate) (pEVA) having vinyl acetate concentrations of between about 10% and about 50% (12%, 14%, 18%, 25%, 33% versions are commercially available), in the form of beads, pellets, granules, etc. pEVA co-polymers with lower percent vinyl acetate become increasingly insoluble in typical solvents, whereas those with higher percent vinyl acetate become decreasingly durable.

When matrix strength or durability is required for a particular application, high efficiency is again a necessary characteristic of an initiation system. When a matrix-forming system is initiated, the free radical polymerization of the system is propagated until gelation and vitrification of the polymerizing system render the diffusion of the elements of the matrix-forming system too difficult. Therefore, the higher the efficiency of the initiation system, the more complete the polymerization resulting in the formation of stronger, more durable matrices. The polymeric initiation systems described in this invention provide a higher degree of efficiency, without the use of accelerants, than is attainable using nonpolymer-bound, low molecular weight initiators.

In another embodiment, the polymeric initiator comprises a polymeric backbone with pendent initiator groups and pendent reactive or affinity groups. These reactive or affinity groups enable the polymeric initiator to bind to target groups on surfaces of interest. This allows the polymeric initiator to bind to the surface of interest. In this manner, interfacial polymerization of macromers can be accomplished. A solution of polymeric initiator-containing pendent reactive or affinity groups is applied to a surface with target sites. The reactive or affinity groups on the polymeric initiator react with the sites on the surface causing the polymeric initiator to bind to the surface. Excess polymeric initiator can then be washed away. A solution of a polymerizable macromer is then applied to the surface. When light energy in applied to the system, a free radical polymerization reaction is initiated only at the surface of interest. By varying the concentration of the polymerizable macromer and the illumination time, the thickness and crosslink density of the resulting matrix on the surface can be manipulated. Generally, there are two methods by which an initiator group can be incorporated into a polymeric backbone. The first method involves the formation of a monomer which includes the initiator. This can be accomplished readily using standard chemical reactions. For example, the acid chloride analog of an initiator can be reacted with an amine-containing monomer, to form a monomer which contains the initiator. The second method of incorporating initiator groups into a polymeric backbone involves coupling a reactive analog of the initiator with a preformed polymer. For example, an acid chloride analog of an initiator can be reacted with a polymer containing pendent amine groups forming a polymer bearing pendent initiator groups.

An exemplary polymer mixture includes mixtures of pBMA and pEVA. This mixture of polymers can be used with absolute polymer concentrations (i.e., the total combined concentrations of both polymers in the coating material), of between about 0.25 wt. % and about 99 wt. %. This mixture can also be used with individual polymer concentrations in the coating solution of between about 0.05 wt. % and about 99 wt. %. In one embodiment the polymer mixture includes pBMA with a molecular weight of from 100 kilodaltons to 900 kilodaltons and a pEVA copolymer with vinyl acetate content of from 24 to 36 weight percent. In an embodiment the polymer mixture includes pBMA with a molecular weight of from 200 kilodaltons to 300 kilodaltons and a pEVA copolymer with vinyl acetate content of from 24 to 36 weight percent. The concentration of the active agent or agents dissolved or suspended in the coating mixture can range from 0.01 to 99 percent, by weight, based on the weight of the final coating material.

Second polymers can also comprise one or more polymers selected from the group consisting of (i) poly(alkylene-co-alkyl(meth)acrylates, (ii) ethylene copolymers with other alkylenes, (iii) polybutenes, (iv) diolefin derived non-aromatic polymers and copolymers, (v) aromatic group-containing copolymers, and (vi) epichlorohydrin-containing polymers.

Poly(alkylene-co-alkyl(meth)acrylates) include those copolymers in which the alkyl groups are either linear or branched, and substituted or unsubstituted with non-interfering groups or atoms. Such alkyl groups can comprise from 1 to 8 carbon atoms, inclusive. Such alkyl groups can comprise from 1 to 4 carbon atoms, inclusive. In an embodiment, the alkyl group is methyl. In some embodiments, copolymers that include such alkyl groups can comprise from about 15% to about 80% (wt) of alkyl acrylate. When the alkyl group is methyl, the polymer contains from about 20% to about 40% methyl acrylate in some embodiments, and from about 25% to about 30% methyl acrylate in a particular embodiment. When the alkyl group is ethyl, the polymer contains from about 15% to about 40% ethyl acrylate in an embodiment, and when the alkyl group is butyl, the polymer contains from about 20% to about 40% butyl acrylate in an embodiment.

Alternatively, second polymers can comprise ethylene copolymers with other alkylenes, which in turn, can include straight and branched alkylenes, as well as substituted or unsubstituted alkylenes. Examples include copolymers prepared from alkylenes that comprise from 3 to 8 branched or linear carbon atoms, inclusive. In an embodiment, copolymers prepared from alkylene groups that comprise from 3 to 4 branched or linear carbon atoms, inclusive. In a particular embodiment, copolymers prepared from alkylene groups containing 3 carbon atoms (e.g., propene). By way of example, the other alkylene is a straight chain alkylene (e.g., 1-alkylene). Exemplary copolymers of this type can comprise from about 20% to about 90% (based on moles) of ethylene. In an embodiment, copolymers of this type comprise from about 35% to about 80% (mole) of ethylene. Such copolymers will have a molecular weight of between about 30 kilodaltons to about 500 kilodaltons. Exemplary copolymers are selected from the group consisting of poly(ethylene-co-propylene), poly(ethylene-co-1-butene), polyethylene-co-1-butene-co-1-hexene) and/or poly(ethylene-co-1-octene).

"Polybutenes" include polymers derived by homopolymerizing or randomly interpolymerizing isobutylene, 1-butene and/or 2-butene. The polybutene can be a homopolymer of any of the isomers or it can be a copolymer or a terpolymer of any of the monomers in any ratio. In an embodiment, the polybutene contains at least about 90% (wt) of isobutylene or 1-butene. In a particular embodiment, the polybutene contains at least about 90% (wt) of isobutylene. The polybutene may contain non-interfering amounts of other ingredients or additives, for instance it can contain up to 1000 ppm of an antioxidant (e.g., 2,6-di-tert-butyl-methylphenol). By way of example, the polybutene can have a molecular weight between about 150 kilodaltons and about 1,000 kilodaltons. In an embodiment, the polybutene can have between about 200 kilodaltons and about 600 kilodaltons. In a particular embodiment, the polybutene can have between about 350 kilodaltons and about 500 kilodaltons. Polybutenes having a molecular weight greater than about 600 kilodaltons, including greater than 1,000 kilodaltons are available but are expected to be more difficult to work with.

Additional alternative second polymers include diolefin-derived, non-aromatic polymers and copolymers, including those in which the diolefin monomer used to prepare the polymer or copolymer is selected from butadiene ($CH_2$=CH—CH=$CH_2$) and/or isoprene ($CH_2$=CH—C($CH_3$)=$CH_2$). In an embodiment, the polymer is a homopolymer derived from diolefin monomers or is a copolymer of diolefin monomer with non-aromatic mono-olefin monomer, and optionally, the homopolymer or copolymer can be partially hydrogenated. Such polymers can be selected from the group consisting of polybutadienes prepared by the polymerization of cis-, trans- and/or 1,2-monomer units, or from a mixture of all three monomers, and polyisoprenes prepared by the polymerization of cis-1,4- and/or trans-1,4-monomer units. Alternatively, the polymer is a copolymer, including graft copolymers, and random copolymers based on a non-aromatic mono-olefin monomer such as acrylonitrile, and an alkyl(meth)acrylate and/or isobutylene. In an embodiment, when the mono-olefin monomer is acrylonitrile, the interpolymerized acrylonitrile is present at up to about 50% by weight; and when the mono-olefin monomer is isobutylene, the diolefin is isoprene (e.g., to form what is commercially known as a "butyl rubber"). Exemplary polymers and copolymers have a molecular weight between about 150 kilodaltons and about 1,000 kilodaltons. In an embodiment, polymers and copolymers have a molecular weight between about 200 kilodaltons and about 600 kilodaltons.

Additional alternative second polymers include aromatic group-containing copolymers, including random copolymers, block copolymers and graft copolymers. In an embodiment, the aromatic group is incorporated into the copolymer via the polymerization of styrene. In a particular embodiment, the random copolymer is a copolymer derived from copolymerization of styrene monomer and one or more monomers selected from butadiene, isoprene, acrylonitrile, a $C_1$-$C_4$ alkyl(meth)acrylate (e.g., methyl methacrylate) and/or butene. Useful block copolymers include copolymer containing (a) blocks of polystyrene, (b) blocks of an polyolefin selected from polybutadiene, polyisoprene and/or polybutene (e.g., isobutylene), and (c) optionally a third monomer (e.g., ethylene) copolymerized in the polyolefin block. The aromatic group-containing copolymers contain about 10% to about 50% (wt.) of polymerized aromatic monomer and the molecular weight of the copolymer is from about 300 kilodaltons to about 500 kilodaltons. In an embodiment, the molecular weight of the copolymer is from about 100 kilodaltons to about 300 kilodaltons.

Additional alternative second polymers include epichlorohydrin homopolymers and poly(epichlorohydrin-co-alkylene oxide) copolymers. In an embodiment, in the case of the copolymer, the copolymerized alkylene oxide is ethylene oxide. By way of example, epichlorohydrin content of the epichlorohydrin-containing polymer is from about 30% to 100% (wt). In an embodiment, epichlorohydrin content is from about 50% to 100% (wt). In an embodiment, the epichlorohydrin-containing polymers have a molecular weight from about 100 kilodaltons to about 300 kilodaltons.

Non-degradable polymers can also include those described in U.S. Pat. App. No. 60/703,555, entitled "DEVICES, ARTICLES, COATINGS, AND METHODS FOR CONTROLLED ACTIVE AGENT RELEASE OR HEMOCOMPATIBILITY", the contents of which is herein incorporated by reference. As a specific example, non-degradable polymers can include random copolymers of butyl methacrylate-co-acrylamido-methyl-propane sulfonate (BMA-AMPS). In some embodiments, the random copolymer can include AMPS in an amount equal to about 0.5 mol. % to about 40 mol.

Specific embodiments of the copolymer include random copolymers of butyl methacrylate-co-acrylamido-methyl-propane sulfonate (pBMA-co-AMPS). In certain embodiments, the random copolymer can include AMPS at about 0.5 to about 30 mol-%, about 1 to about 20 mol-%, or about 2 to about 10 mol-%. In certain embodiments, the random copolymer can include AMPS at about 0.5 to about 40 mol-%, about 20 to about 40 mol-%, about 25 to about 35 mol-%, about 25 to about 30 mol-%, or about 30 mol-%.

An embodiment of a polymer including an effective amount of monomeric unit or monomeric units including polar moieties and at least one second monomeric unit (without charged moiety) can be represented, for example, by Formula A:

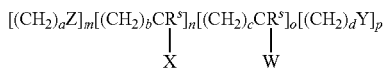

In Formula A: Each [ ] moiety represents a monomeric unit present in the polymer, which can be present in any order, e.g., randomly. Each $R^s$ is independently H or $CH_3$. Each of a, b, c, and d is independently 1-4, 1-3, 1-2, 1, 2, or 3.

Each X and Z is independently a polar moiety. For example, in an embodiment, X can be or include a methyl propane sulfonate moiety (e.g., amido isobutyl sulfonate ($—C(O)NHC(CH_3)_2CH_2SO_3H$, the pendant moiety in the monomer AMPS)). For example, in an embodiment, X can be or include a methyl propane sulfonate moiety and Z is absent (m=0). In certain embodiments, X can be or include a carboxyl containing moiety, a quaternary ammonium containing moiety, a pyridinium containing moiety, combinations thereof, or the like.

Each W and Y is independently a group that is not a charged moiety. W or Y can be or include, for example, a polar or non-polar moiety. W or Y can be or include, for example, alkyl, aryl, methylene, amide, methyl, alcohol, ether, amide, ester, carbamate, carbonate, combinations thereof, or the like. In an embodiment, W can be or include a $—C(O)O—(CH_2)_3 CH_3$ moiety (the pendant moiety of the monomer butyl methacrylate).

In Formula A, each of m, n, o, and p represents the mole fraction of the corresponding monomeric unit in the polymer, and m+n represents an effective mole fraction. For example, m+n can be about 0.5 to about 35 mol-%, about 1 to about 20 mol-%, or about 2 to about 10 mol-%. By way of further example, m+n can be about 1.5 mol-%, about 3 mol-%, or about 9 mol-%. Either m or n can be zero, but m+n>0. The present polymer can include any of these ranges or amounts not modified by about or any of these quantities individually. Either o or p can be zero, but o+p>0.

Suitable random copolymers can include polar monomeric units such as water soluble monomeric units. Water soluble monomeric units include those listed as water soluble in the Polymer Handbook (Branderup and Immergut, eds.), 3$d$ Edition (1989) or later, John Wiley and Sons, NY. Suitable random copolymers are soluble in organic solvent.

Suitable random copolymers can include water soluble polar monomeric units such as a water soluble N-substituted acrylamide including a polar or charged substituent (e.g., a cationic or anionic substituent), a water soluble acrylic acid ester including a polar or charged substituent (e.g., a cationic or anionic substituent), a water soluble carboxyl containing monomeric unit, a water soluble quaternary ammonium containing monomeric unit, combinations thereof, or the like. Suitable random copolymers can include an N-substituted acrylamide including a polar substituent such as acrylamido-methyl propane sulfonate (AMPS). Suitable random copolymers can include an N-substituted acrylamide including a charged substituent such as an alkali metal (e.g., sodium) salt of acrylamido-methyl propane sulfonate (AMPS). Suitable random copolymers can include an acrylic acid ester including a polar substituent such as 3-sulfopropyl(meth)acrylate. Suitable random copolymers can include an acrylic acid ester including a charged substituent such as an alkali metal (e.g., sodium) salt of 3-sulfopropyl(meth)acrylate. Suitable random copolymers can include a water soluble N-substituted acrylamide including a cationic substituent such as a water soluble quaternary ammonium substituted acrylamide or methacrylamide.

Suitable random copolymers can include as the second monomeric unit an acrylate or methacrylate. Suitable second monomeric units include N,N-dimethylacrylamide, N,N-diethylacrylamide, N-isopropylacrylamide, N-t-butylacrylamide, N-octylacrylamide, N-cyclohexylacrylamide, N-phenylacrylamide, N-benzylacrylamide, N-methylmethacrylamide, N-ethylmethacrylamide, N,N-dimethylmethacrylamide, N,N-diethylmethacrylamide, alkyl or aryl acrylate, alkyl or aryl methacrylate, vinylmethylether, combinations thereof, or the like. Suitable second monomeric units include a methacrylate, for example, butyl methacrylate.

Suitable polymer backbones including uncharged polar moieties include polyethers (e.g., polyethylene glycol, polypropylene glycol), substituted polyalkyleneimines (e.g., substituted polyethyleneimine), and the like. Suitable random copolymers include butyl methacrylate-co-acrylamido-methyl-propane sulfonate (PBMA-co-AMPS). The copolymer can include polar monomeric unit at about 0.5 to about 30 mol-%, about 1 to about 20 mol-%, or about 2 to about 10 mol-%. The copolymer can include polar monomeric unit at about 1.5 mol-%, about 3 mol-%, or about 9 mol-%. The copolymer can include second monomeric unit at about 70 to about 99.5 mol-%, about 80 to about 99 mol-%, or about 90 to about 98 mol-%, or about 85 to about 95 mol-%. The copolymer can include second monomeric unit at about 98.5 mol-%, about 97 mol-%, or about 91 mol-%. The present polymer can include any of these ranges or amounts not modified by about or any of these quantities individually.

In an embodiment, the copolymer can include polar monomeric unit at an amount such that the copolymer, when wetted, does not form a hydrogel. In an embodiment, the copolymer can include polar monomeric unit at an amount such that the copolymer, when wetted, does not expand. In an embodiment, the copolymer can include polar monomeric unit at an amount such that the copolymer, when wetted, does not expand significantly.

In some embodiments the present invention includes polymeric layers wherein the polymers are selected so that the solubility of drugs and polymers are closely matched to control elution profiles. In certain embodiments various methacrylate containing polymers can be used, including hydrophobic and hydrophilic polymers. Suitable materials include, for example, butyl methacrylates, in particular hydrophobic butyl methacrylates and hydrophobic hexyl methacrylates. Other suitable materials can include hydrophilic vinyl pyrrolidinones, and vinyl acetates. Combinations of these materials is possible, including combinations of hydrophobic hexyl methacrylates with the hydrophilic vinyl pyrrrolidnone and a vinyl acetate. Vinyl acetates from C13 to C25 are suitable in some embodiments, as are those from C17 to C21, notably including C19. Notably, polyvinyl pyrrolidinones are suitable for various embodiments. The polyvinyl pyrrolidinones can be used to provide a rapid increase in drug elution.

In another embodiment of the shell coatings or articles, a plurality of natural biodegradable polysaccharides are crosslinked to each other via coupling groups that are pendent from the natural biodegradable polysaccharide (i.e., one or more coupling groups are chemically bonded to the polysaccharide). In some aspects, the coupling group on the natural biodegradable polysaccharide is a polymerizable group. In a free radical polymerization reaction the polymerizable group can crosslink natural biodegradable polysaccharides together in the composition, thereby forming a natural biodegradable polysaccharide matrix, which can be a portion of a coating, an in-vivo formed matrix, or the body member of a medical implant.

The natural biodegradable polysaccharides described herein are non-synthetic polysaccharides that can be associated with each other to form a matrix, which can be used as a coating or as an article, for example, a medical implant or an in-vivo formed matrix. The natural biodegradable polysaccharides can also be enzymatically degraded, but offer the advantage of being generally non-enzymatically hydrolytically stable. This is particularly advantageous for bioactive agent delivery, as in some aspects the invention provides coatings or articles capable of releasing the bioactive agent under conditions of enzyme-mediated degradation, but not by diffusion. Therefore, the kinetics of bioactive agent release from the coatings or articles of the invention are fundamentally different than those of coatings prepared from synthetic biodegradable materials, such as poly(lactides).

Natural biodegradable polysaccharides include polysaccharide and/or polysaccharide derivatives that are obtained from natural sources, such as plants or animals. Exemplary natural biodegradable polysaccharides include amylose, maltodextrin, amylopectin, starch, dextran, hyaluronic acid, heparin, chondroitin sulfate, dermatan sulfate, heparan sulfate, keratan sulfate, dextran sulfate, pentosan polysulfate, and chitosan. Preferred polysaccharides are low molecular weight polymers that have little or no branching, such as those that are derived from and/or found in starch preparations, for example, amylose and maltodextrin.

Because of the particular utility of the amylose and maltodextrin polymers, in some aspects natural biodegradable polysaccharides are used that have an average molecular weight of 500,000 Da or less, 250,000 Da or less, 100,000 Da or less, or 50,000 Da or less. In some aspects the natural biodegradable polysaccharides have an average molecular weight of 500 Da or greater. In some aspects the natural biodegradable polysaccharides have an average molecular weight in the range of about 1000 Da to about 10,000 Da. Natural biodegradable polysaccharides of particular molecular weights can be obtained commercially or can be prepared, for example, by acid hydrolysis and/or enzymatic degradation of a natural biodegradable polysaccharide preparation, such as starch. The decision of using natural biodegradable polysaccharides of a particular size range may depend on factors such as the physical characteristics of the coating composition (e.g., viscosity), the desired rate of degradation of the coating, the presence of other optional moieties in the coating composition (for example, bioactive agents, etc.), etc. The coating is further described in U.S. application Ser. No. 11/271,273, entitled Coatings including Natural Biodegradeable Polysaccharides and Uses Thereof, the disclosure of which is incorporated by reference.

The present copolymer composition can be applied to a substrate or device using known methods. For example, the copolymer can be mixed with active agent and solvent and applied to a substrate or device by spraying (e.g., aerosol or ultrasonic), dipping, or with an ultrasonic coater. In some embodiments, the present composition can include a preformed polymer. For example, an active agent may be mixed with a preformed polymer and then deposited on a substrate. The method can include drying the device after applying the copolymer composition.

The beads were dipped in a basecoat of 50%, by weight, polyethylene vinyl acetate and 50% w/w of tobramycin in a chloroform solvent. The coating took place at room temperature with immersion for five seconds. The base coat was dried for two hours at room temperature in a vacuum. The topcoat was 95%, by weight, poly(butylmethacrylate) and tobramycin 5% w/w dissolved in isopropanol. The topcoat was dried for two hours in vacuum. The completed beads were allowed to further dry overnight in a hood. Beads were sterilized by ethylene oxide.

The copolymer composition can be applied at relative humidity of, for example, about 5% to about 75%, about 5% to about 50%, about 5% to about 35%, or about 5% to about 10%. Although not limiting to the present invention, it is believed that applying the present copolymer composition at a higher relative humidity will increase the rate of active agent release compared to a lower humidity.

In an example embodiment, the bead substrate used comprised poly(undecylamide) including 20 weight percent of barium sulfate ($BaSO_4$). The suture material was uncoated poly(hexamethyleneadipamide). In particular, the poly(hexamethyleneadipamide) was substantially free of silicone.

The bead substrate and suture material was subsequently coated with a basecoat containing approximately 1:1 ratio of tobramycin to photo-poly[vinylpyrrolidone] dissolved in a solution of 50 percent water and 50 percent isopropanol at a loading rate of 100 mg/ml of the tobramycin and photo-poly [vinylpyrrolidone] to the solution of water and isopropyl alcohol.

The coated beads and substrate were allowed to dry for greater than one hour at ambient conditions, and then subjected to UV cure for three minutes The objective was to have a Tobramycin drug load of approximately 1.0 to 1.5 mg per bead.

After the base coat was applied, a middle coat was formed using a combination of 5 parts PBMA to 95 parts PEVA to 5 parts photoreagent tetrakis(4-benzophenylmethoxymethyl) methane to 15 parts photo-poly[vinylpyrrolidone] added at a rate of 115 mg/mL in chloroform. This coating was dried for greater than 5 minutes at ambient conditions, and then UV cured for 3 minutes. Thereafter, a top coat of PBMA was applied at a rate of 75 mg/mL in isopropanol. The top coat was dried for greater than 30 minutes at ambient conditions.

An example desirable elution profile for the active agent eluted from the device is rapid initial elution, and continued high levels of elution for about 72 hours, resulting in local tissue concentrations within normally acceptable clinical limits. In certain embodiments, a dose of about 500 to 2000 mcg per bead is desired, which allows the device to achieve an immediate area concentration of at least 40 mcg/ml.

Generally it is desirable for the active agent to elute at a rate so as to produce an active agent level that is approximately ten times the minimum inhibitory concentration (MIC). The system-wide toxic concentration of tobramycin, for example, is about 400 mcg/ml, and the effective concentration to actively control bacteria is about 4 mcg/ml or lower.

The present invention seeks to have local active agent levels of about 10 times the effective systemic concentration. Thus, in the case of tobramycin, an example target local concentration is about 40 mcg/ml. In one example, each 7 mm (radius 3.5 mm) bead is 0.18 ml of space for volume of a sphere, 60 beads are approximately 12 ml of volume). If wound space is an additional 25 ml, then 30 mg (500 mcg/bead) of tobramycin is desirably released-immediately into the 25 ml volume for a potential concentration of 1200 mcg/ml.

In certain embodiments it is desirable to have relatively high levels of the total active agent elute quickly from the device. For example, within the first 48 hours, it is desirable in some implementations for at least 50 percent, more desirably at least 60 percent, and even more desirably at least 70 percent of the active agent to have eluted, so as to provide high localized concentrations of active agent. Generally it is desirable that a high percentage of the active agent elute from the device, typically at least 50 percent of the active agent, more desirably at least 70 percent of the active agent, and even more desirably 80 percent or more of the active agent.

Figure 8A:
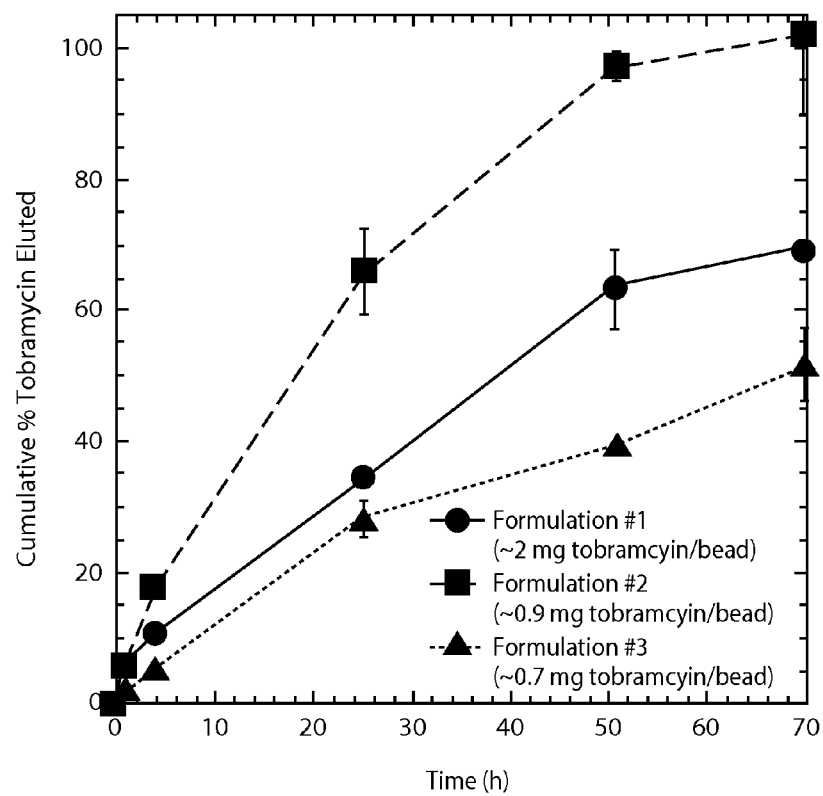
FIG. 8A shows an elution profile for tobramycin from a coating containing pEVA and pBMA over 72 hours, at various tobramycin loading levels per bead, showing elution as a percent of total tobramycin present.
Figure 8B:
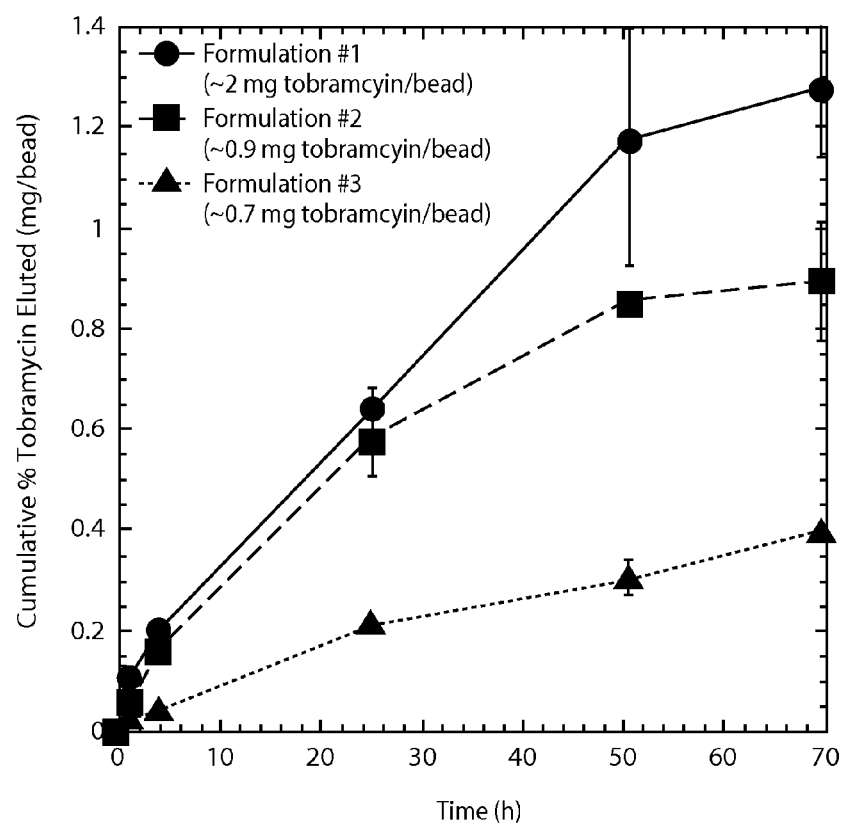
FIG. 8B shows an elution profile for tobramycin from a coating containing pEVA and pBMA over 72 hours, at various tobramycin loading levels per bead, showing elution as a milligrams of tobramycin eluted per bead.

In reverence now to example formulations and elution profiles, FIGS. 8A and 8B show example elution profiles for three formulations. Substrates were polyamide beads on polyamide suture material. The basecoat was 1:1 (wt/wt) photo-poly[vinylpyrrolidone]:tobramycin for 100 mg/mL total solids in a 50/50 water/isopropanol solution. The beads were dried for approximately 2 hours, then UV cured for 3 minutes. A midcoat was 5:95:5:10 PBMA:PEVA: tetrakis(4-benzophenylmethoxymethyl)methane photo-poly[vinylpyrrolidone, 115 mg/mL in chloroform was applied. The beads were dried approximately 30 minutes, then UV cured for 3 minutes. The topcoat was PBMA applied at 75 mg/mL in isopropanol. The differences among the elution rates of the formulations was achieved by varying the amount of coating placed on the device. Formulation 1 contained approximately 2 mg of tobramycin per bead, formulation 2 contained approximately 0.9 mg of tobramycin per bead, and formulation 3 contained approximately 0.7 mg of tobramycin per bead.

FIG. 8A shows an elution profile for tobramycin from a coating containing pEVA and pBMA over 72 hours, at various tobramycin loading levels per bead, showing elution as a percent of total tobramycin present. FIG. 8B shows an elution profile for tobramycin from a coating containing pEVA and pBMA over 72 hours, at various tobramycin loading levels per bead, showing elution measured as milligrams of tobramycin eluted per bead. For all plots, elution was carried out in PBS, pH 7.4, 37° C. The amount of tobramycin eluted was quantified by reacting eluted tobramycin with the fluorescent dye fluorescamine, which fluoresces only when reacted with the free amines of the tobramycin. The fluorescence intensity (Ex=400 nm, Em=460 nm) was compared to a standard curve to determine the amount of tobramycin eluted.

Figure 9A:
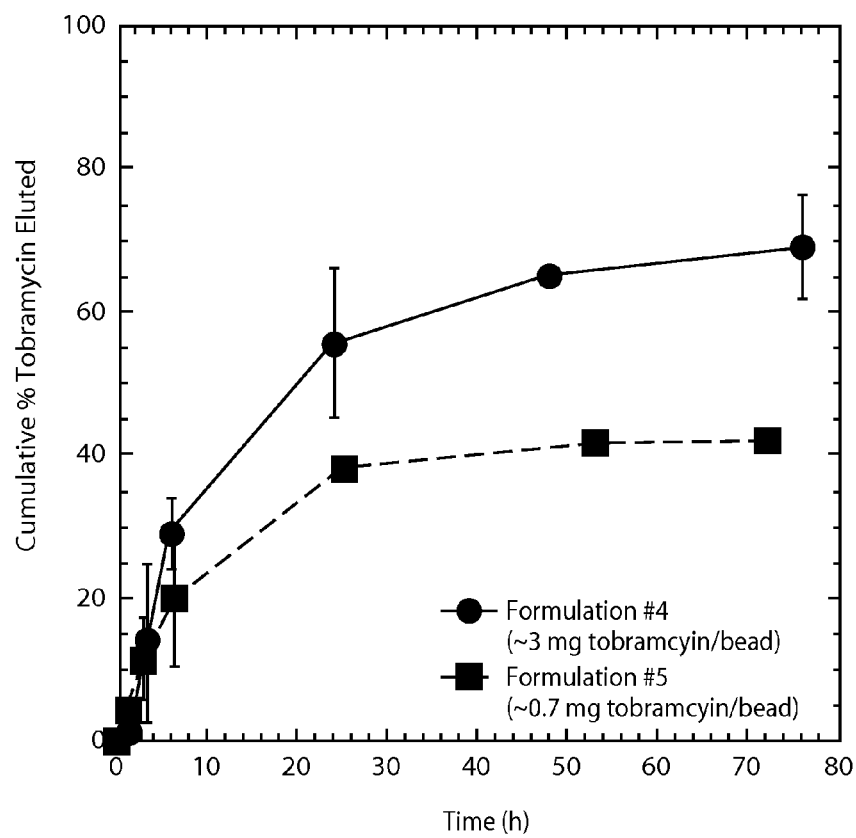
FIG. 9A shows an elution profile for tobramycin from a coating containing pEVA and pBMA over 72 hours, at various tobramycin loading levels per bead, showing elution as a percent of total tobramycin present.
Figure 9B:
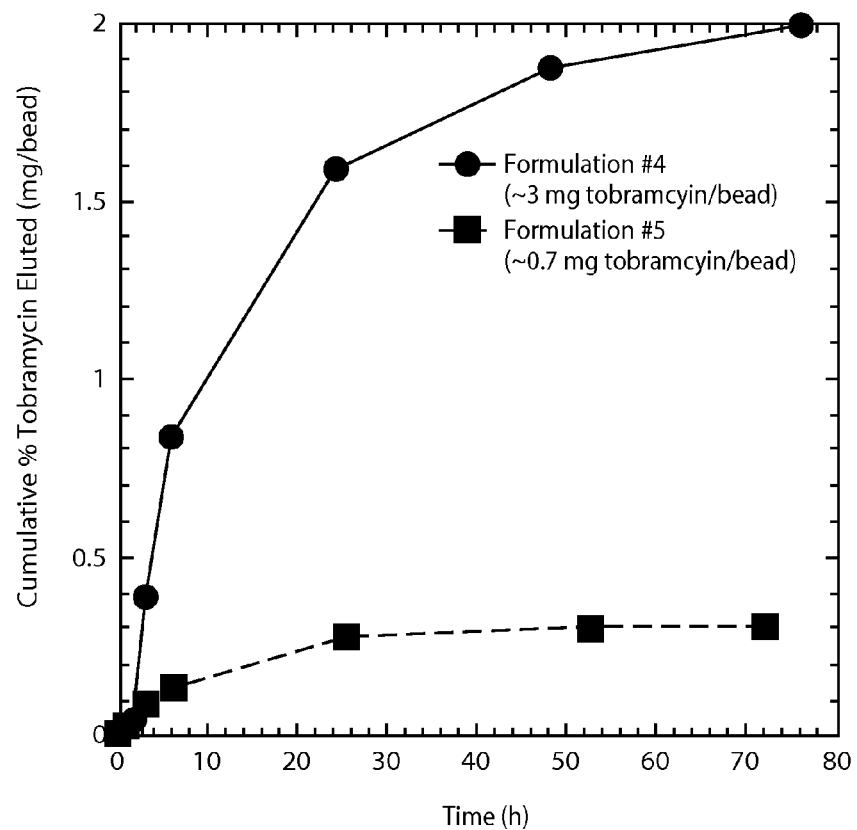
FIG. 9B shows an elution profile for tobramycin from a coating containing pEVA and pBMA over 72 hours, at various tobramycin loading levels per bead, showing elution as a milligrams of tobramycin eluted per bead.

FIGS. 9A and 9B show example elution profiles for two formulations. Substrates were polyamide beads on polyamide sutures. The basecoat was tobramycin (with no polymer present). In formulation 4 the tobramycin was applied as a solution of 300 mg/mL of tobramycin in 67/33 water/isopropanol solution. In formulation 5 the tobramycin was applied as a solution of 70 mg/mL tobramycin in a 50/50 water/isopropanol solution. The beads were dried for approximately 2 hours and then coated with 5:95 PBMA:PEVA, 100 mg/mL in chloroform. The beads were dried approximately 1 hour, then coated with PBMA, 100 mg/mL in IPA. The differences between the elution rates of the formulations was achieved by varying the amount of drug or coating placed on the device.

FIG. 9A shows an elution profile for tobramycin from a coating containing pEVA and pBMA over 72 hours, at various tobramycin loading levels per bead, showing elution as a percent of total tobramycin present. FIG. 9B shows an elution profile for tobramycin from a coating containing pEVA and pBMA over 72 hours, at various tobramycin loading levels per bead, showing elution as milligrams of tobramycin eluted per bead.

Figure 10A:
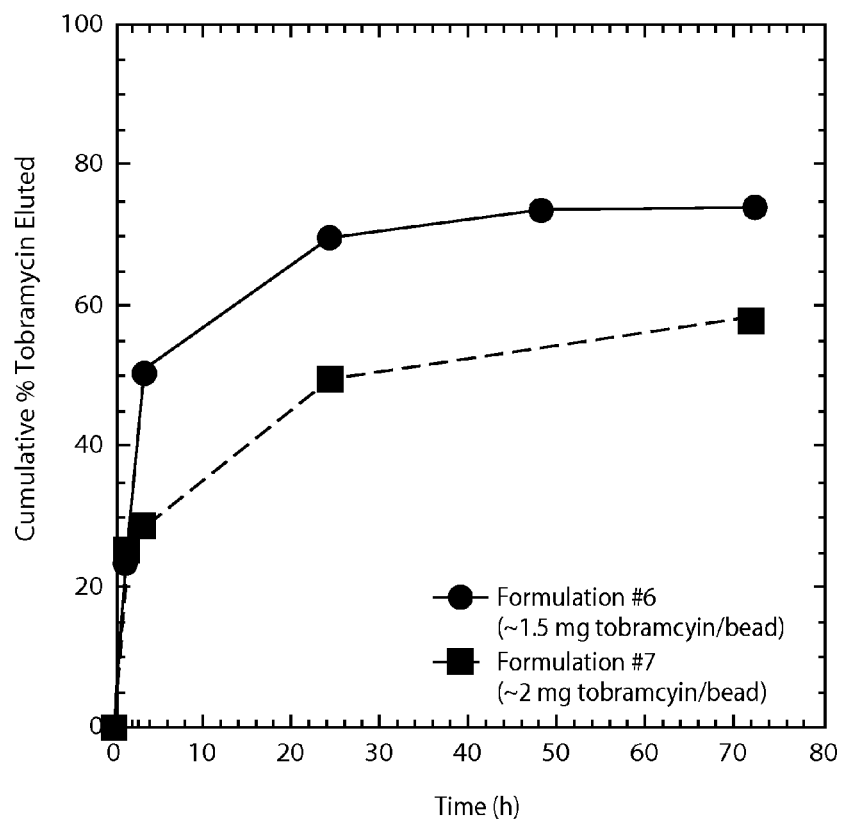
FIG. 10A shows an elution profile for tobramycin from a coating containing pEVA and pBMA over 72 hours, at various tobramycin loading levels per bead, showing elution as a percent of total tobramycin present.
Figure 10B:
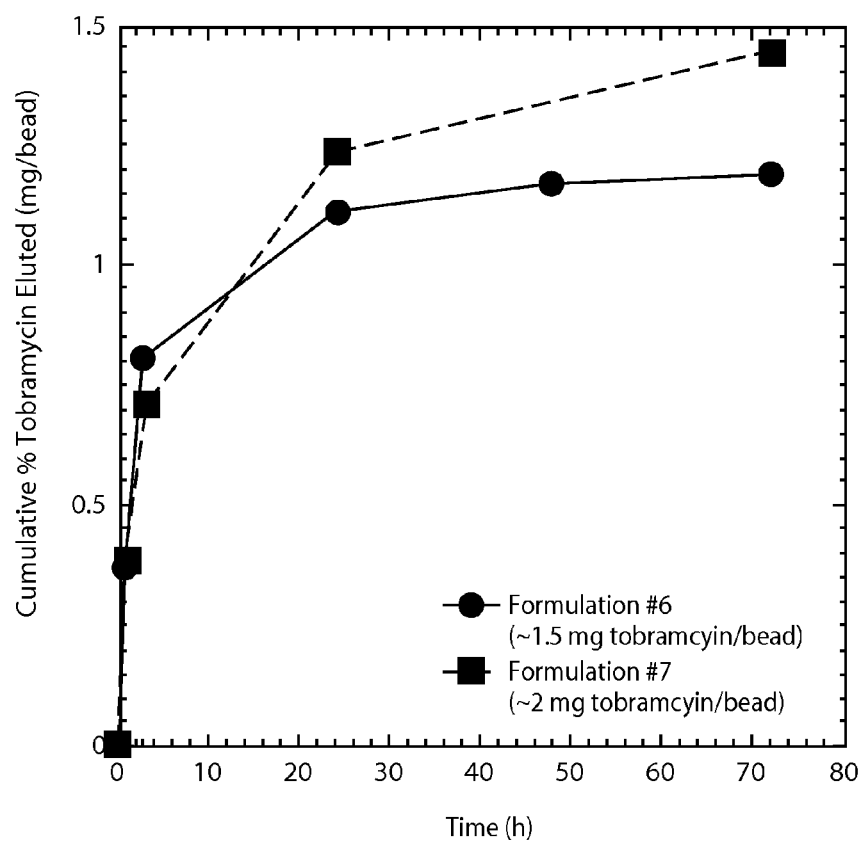
FIG. 10B shows an elution profile for tobramycin from a coating containing pEVA and pBMA over 72 hours, at various tobramycin loading levels per bead, showing elution as a milligrams of tobramycin eluted per bead.

FIGS. 10A and 10B show example elution profiles for two formulations. Substrates were PMMA beads on polyethylene linking material. Tobramycin was mixed with chloroform (a non-solvent for tobramycin) and ball-milled for more than 2 hours at room temperature to reduce the particle size of the tobramycin. The tobramycin was mixed with PEVA in chloroform to produce a suspension of tobramycin particles in a solution of PEVA. The ratio of tobramycin to PEVA was 1:2 for formulation number 6 and 1:1 for formulation number 7. Total solids concentration was 100 or 150 mg/mL.

The mixture formed a viscous suspension that gelled when undisturbed for hours, but flowed when shaken. Beads were dip-coated with this mixture and dried for approximately 1 hour under vacuum at room temperature. A topcoat of PBMA was applied at a rate of 100 mg/mL in tetrahydrofuran or 9:1 PBMA:tobramycin particles in 100 mg/mL in isopropanol. The topcoat was dried 1 hour under vacuum at room temperature.

Figure 11:
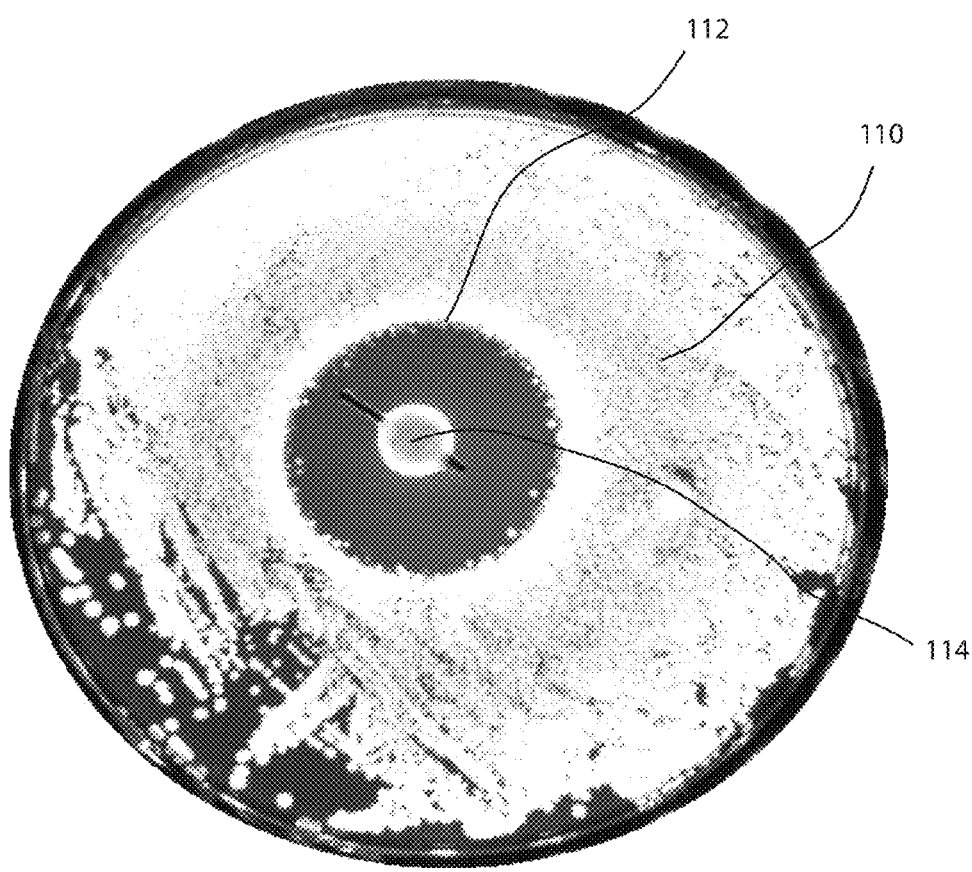
FIG. 11 shows a zone of inhibition from a bead made in accordance with an implementation of the present invention.

Differences between the elution rates of the formulations was achieved by varying the amount of drug or coating placed on the device. FIG. 10A shows an elution profile for tobramycin from a coating containing pEVA and pBMA over 72 hours, at various tobramycin loading levels per bead, showing elution as a percent of total tobramycin present. FIG. 10B shows an elution profile for tobramycin from a coating containing pEVA and pBMA over 72 hours, at various tobramycin loading levels per bead, showing elution as milligrams of tobramycin eluted per bead The effect of such elution of active agent is apparent, for example, from FIG. 11, in which a zone of inhibition 112 of microbe growth is shown around a bead 110 within a Petri dish 114.

The embodiments of the present invention described herein are not intended to be exhaustive or to limit the invention to the precise forms disclosed in the following detailed description. Rather, the embodiments are chosen and described so that others skilled in the art can appreciate and understand the principles and practices of the present invention. All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

We claim:

1. A removable wound spacer packing device, said wound spacer packing device comprising:
   a plurality of beads arranged along a flexible textured polyamide connector material, each of said beads comprising:
   a polyamide core;
   a first layer outside said core, said first layer containing a bioactive agent and a polymeric material derived from poly[vinylpyrrolidone], wherein said polymeric material is crosslinked to the core material;
   a second layer outside said first layer, said second layer comprising poly(butylmethacrylate) and poly(ethylene-co-vinyl acetate), wherein the second layer outside the core is crosslinked to the first layer outside the core; and
a third layer outside said first layer, said third layer comprising poly(butylmethacrylate).

2. The removable wound spacer packing device of claim 1, wherein the second layer further comprises poly (vinylpyrrolidone).

3. The removable wound spacer packing device of claim 1, wherein the bioactive agent is selected from the group consisting of tobramycin, tobramycin sulfate, vancomycin, amikacin, gentamicin, kanamycin, neomycin, tigecycline, netilmicin, paromomycin, streptomycin, and apramycin and combinations thereof.

4. The removable wound spacer packing device of claim 1, wherein the bioactive agent comprises tobramycin sulfate.

5. The removable wound spacer packing device of claim 1, wherein the poly(ethylene-co-vinyl acetate) is selected from the group consisting of poly(ethylene-co-vinyl acetate) polymers having vinyl acetate concentrations of between about 10% and about 50% by weight.

6. The removable wound spacer packing device of claim 1, wherein the bioactive agent comprises a dose of about 500 to 2000 mcg per bead.

7. The removable wound spacer packing device of claim 1, wherein the bioactive agent has an elution profile such that at least 50 percent of the bioactive agent releases from the first, second, and third layers within 72 hours of placement within a wound.

8. The removable wound spacer packing device of claim 1, wherein the bioactive agent has an elution profile such that at least 65 percent of the bioactive agent releases from the first, second, and third layers within 72 hours of placement within a wound.

9. The removable wound spacer packing device of claim 1, wherein the beads are each molded to the connector material with sufficient strength so that the connector material will break under a tension load before the bond between the connector material and polyamide core breaks.

10. The removable wound spacer packing device of claim 1, wherein the cores of the plurality of beads contain barium sulfate.

11. The removable wound spacer packing device of claim 1, wherein only a portion of each bead of the plurality of beads contains barium sulfate.

12. The removable wound spacer packing device of claim 1, wherein the plurality of beads have an average spacing distance that is between 0.8 and 1.2 times the length of the average bead core diameter in contact with the connecting material.

13. The removable wound spacer packing device of claim 1, wherein the flexible polyamide connector material is coated with at least a first layer containing a bioactive agent and a polymeric material derived from poly[vinylpyrrolidone].

14. The removable wound spacer packing device of claim 1, wherein the flexible polyamide connector material is substantially free of silicone.

15. The removable wound spacer packing device of claim 1, wherein the connector material comprises flexile braided suture material.

16. The removable wound spacer packing device of claim 1, wherein the beads are non-spherical.

17. The removable wound spacer packing device of claim 1, wherein the beads have an average volume between 15 and 8,000 cubic millimeters.

18. The removable wound spacer packing device of claim 1, wherein the device volume is from 1 to 150 cubic centimeters.

19. A removable wound spacer packing device, said wound spacer packing device comprising:
a plurality of beads arranged along a flexible textured polyamide connector material, each of said polyamide beads comprising:
a polyamide core containing barium sulfate;
a first layer outside said core, said first layer containing a bioactive agent and a polymeric material derived from poly[vinylpyrrolidone] wherein said polymeric material is crosslinked to the core material;
a second layer outside said first layer, said second layer comprising a material derived from poly(butylmethacrylate), poly(ethylene-co-vinyl acetate) and poly (vinyl pyrrolidone), wherein the second layer outside the core is crosslinked to the first layer outside the core; and
a third layer outside said first layer, said third layer comprising poly(butylmethacrylate).

20. The removable wound spacer packing device of claim 19, wherein the bioactive agent is selected from the group consisting of tobramycin, tobramycin sulfate, vancomycin, amikacin, gentamicin, kanamycin, neomycin, tigecycline, netilmicin, paromomycin, streptomycin, and apramycin and combinations thereof.

21. The removable wound spacer packing device of claim 19, wherein the bioactive agent has an elution profile such that at least 65 percent of the bioactive agent elutes within 72 hours of placement within a wound.

22. The removable wound spacer packing device of claim 19, wherein the poly(ethylene-co-vinyl acetate) is selected from the group consisting of poly(ethylene-co-vinyl acetate) polymers having vinyl acetate concentrations of between about 10% and about 50% by weight.

23. The removable wound spacer packing device of claim 19, wherein the flexible polyamide connector material is coated with at least a first layer containing a bioactive agent and a polymeric material derived from poly[vinylpyrrolidone].

24. A kit for treating a wound, the kit comprising:
at least two removable wound spacer packing devices, each of said wound spacer packing devices comprising a plurality of beads arranged along a flexible textured polyamide connector material, each of said polyamide beads comprising:
a polyamide core containing barium sulfate;
a first layer outside said core, said first layer containing a bioactive agent and a polymeric material derived from poly[vinylpyrrolidone] wherein said polymeric material is crosslinked to the core material;
a second layer outside said first layer, said second layer comprising a material derived from poly(butylmethacrylate), poly(ethylene-co-vinyl acetate) and poly (vinyl pyrrolidone), wherein the second layer outside the core is crosslinked to the first layer outside the core; and
a third layer outside said first layer, said third layer comprising poly(butylmethacrylate); and
a retaining device for holding the at least two removable wound spacer packing devices during storage and prior to application to a wound.

25. The kit for treating a wound of claim 24, wherein at least one of the wound spacer packing devices contains the bioactive agent tobramycin sulfate.

26. The kit for treating a wound of claim 25, wherein at least one of the wound spacer packing devices contains a gram positive bioactive agent.

27. The removable wound spacer packing device of claim 19, wherein the textured suture material comprises braided suture material.

28. The removable wound spacer packing device of claim 24, wherein the textured suture material comprises braided suture material.

* * * * *